United States Patent
Evers et al.

[11] Patent Number: 5,977,067
[45] Date of Patent: Nov. 2, 1999

[54] CYCLOSPORIN DERIVATIVES, THEIR PREPARATION AND THE PHARMACEUTICAL COMPOSITIONS WHICH CONTAIN THEM

[75] Inventors: Michel Evers, La Queue en Brie; Serge Mignani, Chatenay-Malabry; Jean-Christophe Carry, Meudon; Bruno Filoche, Creteil; Georges Bashiardes, Thiais; Claude Bensoussan, Chevilly-Larue; Jean-Christophe Gueguen, Chatenay-Malabry; Jean-Claude Barriere, Bures sur Yvette, all of France

[73] Assignee: Rhone-Poulenc Rorer S.A., Antony Cedex, France

[21] Appl. No.: 09/069,959

[22] Filed: Apr. 30, 1998

[30] Foreign Application Priority Data

Apr. 30, 1997 [FR] France ................... 97 05351

[51] Int. Cl.⁶ .................. A61K 37/02; C07K 5/12
[52] U.S. Cl. ................ 514/11; 514/9; 530/317; 530/321
[58] Field of Search ................. 530/317, 321; 514/9, 11

[56] References Cited

U.S. PATENT DOCUMENTS

| | | | |
|---|---|---|---|
| 4,703,033 | 10/1987 | Seebach | 514/11 |
| 4,771,122 | 9/1988 | Seebach | 530/317 |
| 4,798,823 | 1/1989 | Witzel | 514/11 |
| 4,814,323 | 3/1989 | Andrieu et al. | 514/11 |
| 4,885,276 | 12/1989 | Witzel | 514/11 |

FOREIGN PATENT DOCUMENTS

| | | |
|---|---|---|
| 484281 | 5/1992 | European Pat. Off. |
| 96/03129 | 7/1995 | WIPO |
| WO 9704005 | 2/1997 | WIPO |

OTHER PUBLICATIONS

Bartz, et al, PNAS, USA, vol. 92, pp. 5381–5385, 1995.
Karpas et al, PNAS, USA, vol. 89, pp. 8351–8355, 1992.
Yarchoan, et al, J. Enzyme Inhibition, 1992, vol. 6, pp. 99–111.
Billich et al., "Mode of Action of SDZ NIM 811, a Non-immunosuppressive Cyclosporin A Analog With Activity Against Human Immunodeficiency Virus (HIV) Type 1: Interference With HIV Protein Cyclophilin A Interactions," J. of Virology, 69(4):2451–2461 (1995).

*Primary Examiner*—Cecilia J. Tsang
*Attorney, Agent, or Firm*—Finnegan, Henderson, Farabow, Garrett & Dunner, L.L.P.

[57] ABSTRACT

Cyclosporin derivatives of formula (I) in which R is H or a radical (Ia) or (Ib) as defined herein; R' is a radical (Ic) or (Id) as defined herein; and R" represents H or OH, with the proviso that R and R" are not simultaneously H, and pharmaceutically acceptable salts thereof, when they exist, are disclosed as useful for the treatment and/or prophylaxis of retrovirus infections.

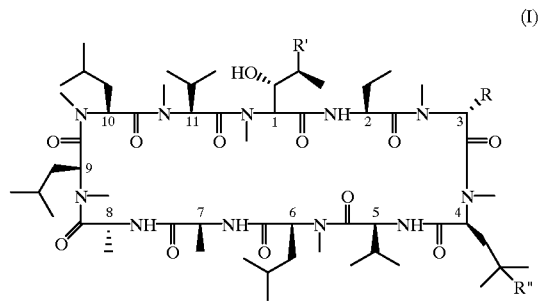

17 Claims, No Drawings

CYCLOSPORIN DERIVATIVES, THEIR PREPARATION AND THE PHARMACEUTICAL COMPOSITIONS WHICH CONTAIN THEM

The present invention relates to novel cyclosporin derivatives of formula (I):

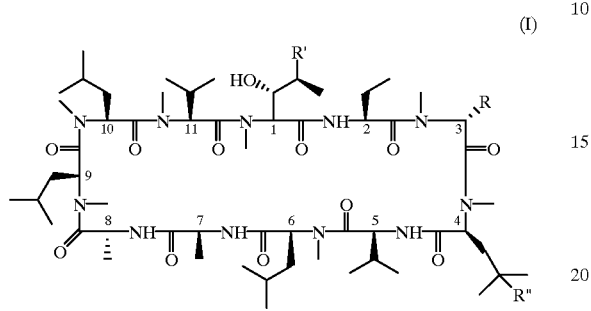

(I)

to their salts, to their preparation and to the pharmaceutical compositions which contain them.

In addition to antibiotic activity, the derivatives of formula (I) are preferably useful in the treatment and/or prophylaxis of retrovirus infections and more particularly of AIDS (acquired immunodeficiency syndrome) and of associated syndromes [ARC (AIDS related complex)].

Cyclosporin derivatives respectively modified at the 1- or 3-position have been previously described as immunosuppressants, in British Patent Application 2,205, 317 and in European Patent EP 194,972.

Cyclosporin derivatives modified at the 1-position by very short chains have been described by S. Bartz in Proc. Natl. Acad. Sci. USA, 92, 5381 (1995) as agents useful in the treatment of AIDS; however, longer chains resulted in the disappearance of the activity.

Variously modified cyclosporin derivatives and in particular the [4'-hydroxy-MeLeu]$^4$-cyclosporin derivative have been previously described in European Patent 484,281 and in Eur. J. Immunol., 17, 1359 (1987). These derivatives are useful in the treatment of AIDS.

It has now been found that the cyclosporin derivatives of formula (1) in which: R is a hydrogen atom or a radical of structure:

—S—Alk—R°    (Ia)

in which

Alk—R° represents a methyl radical, or alternatively

Alk represents a straight- or branched-chain alkylene radical containing 2 to 6 carbon atoms or a cycloalkylene radical containing 3 to 6 carbon atoms and R° represents either a hydrogen atom or a hydroxyl, carboxyl or alkyloxycarbonyl radical, or an —NR$_1$R$_2$ radical in which R$_1$ and R$_2$, which are identical or different, are selected from hydrogen atoms and phenyl, alkyl, alkenyl having 2 to 4 carbon atoms, and cycloalkyl having 3 to 6 carbon atoms radicals, said radicals optionally containing a substituent selected from a halogen atom, alkyloxy, alkyloxycarbonyl, amino, alkylamino and dialkylamino and benzyl and heterocyclyl radicals, said benzyl and heterocyclyl radicals being saturated or unsaturated and containing 5 or 6 ring members and 1 to 3 heteroatoms, or in which R$_1$ and R$_2$ form, together with the nitrogen atom to which they are attached, a 4- to 6-membered heterocycle which can contain another heteroatom chosen from nitrogen, oxygen and sulphur, and which is optionally substituted by an alkyl, phenyl or benzyl radical, or a radical of formula (Ib):

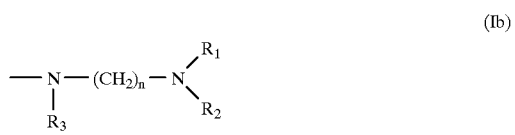

(Ib)

in which R$_1$ and R$_2$ are defined as above, R$_3$ represents a hydrogen atom or an alkyl radical and n is an integer ranging from 2 to 4, R' represents a (Ic) or a (Id) radical:

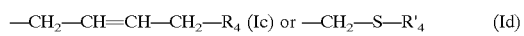
—CH$_2$—CH=CH—CH$_2$—R$_4$ (Ic) or —CH$_2$—S—R'$_4$    (Id)

in which R$_4$ represents an alkylthio, aminoalkylthio, alkylaminoalkylthio, dialkylaminoalkylthio, pyrimidinylthio, thiazolylthio, N-alkylimidazolylthio, hydroxyalkylphenylthio, hydroxyalkylphenyloxy, nitrophenylamino or 2-oxopyrimidin-1-yl radical, and R'$_4$ represents an alkyl radical, and R" represents a hydrogen atom or a hydroxyl radical, with the proviso that R and R" are not simultaneously a hydrogen atom and it being understood that the alkyl portions or radicals defined above are straight or branched and contain 1 to 4 carbon atoms, and their pharmaceutically acceptable salts, when they exist, are particularly advantageous because of their powerful activity.

In the formula (1), when R$_1$ and/or R$_2$ represent heterocyclyl, the heterocyclyl can advantageously be chosen from pyridyl, tetrahydropyridyl, piperidyl, imidazolyl, oxazolyl or thiazolyl.

When R$_1$ and R$_2$ form heterocyclyl with the nitrogen atom to which they are attached, by way of example, the heterocyclyl radical can be chosen from azetidinyl, piperidyl, piperazinyl, N-methylpiperazinyl, N-phenylpiperazinyl, N-benzylpiperazinyl, pyridyl, imidazolyl, morpholino, thiomorpholino, tetrahydropyridyl, methyltetrahydropyridyl (for example 4-methyltetrahydropyridyl) or phenyltetrahydropyridyl (for example 4-phenyltetrahydropyridyl).

According to the present invention, the compounds of formula (I) in which R' is a radical of formula (Ic) can be obtained from the 8'-bromo-3'-acetoxycyclosporin of formula (II):

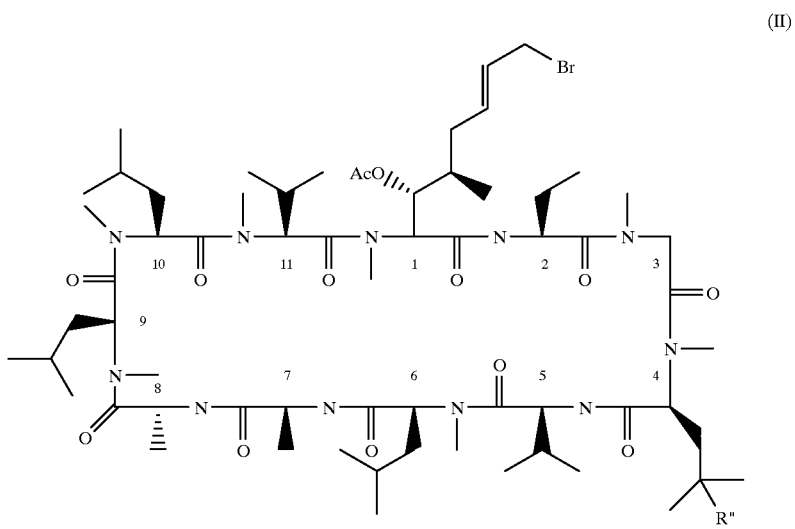

(II)

in which R" is defined as above, by reaction with a thiol of formula (IIIa):

HS—R"₄  (IIIa)

in which R"₄ represents an alkyl, aminoalkyl, alkylaminoalkyl, dialkylaminoalkyl, pyridinyl, thiazolyl, N-alkylimidazolyl or hydroxyalkylphenyl radical, or with a phenol of formula (IIIb):

HO—R'''₄  (IIIb)

in which R'''₄ represents a hydroxyalkylphenyl radical, or an amine of formula (IIIc):

H₂N—R''''₄  (IIIc)

in which R''''₄ represents a nitrophenyl radical or a radical of 2-oxopyrimidine, the reaction being carried out in basic medium, and then removal of the hydroxy-protective acetyl radical, followed, if appropriate, by the subsequent operation of hydroxylation at the 4'-position of the [MeLeu]⁴ residue, when it is desired to obtain a derivative in which R" is hydroxyl and when the reaction has been carried out starting from a cyclosporin derivative in which R" is a hydrogen atom, and/or followed by the subsequent operation of substitution of the chain of formula (Ia), when it is desired to obtain a cyclosporin derivative in which R is other than the hydrogen atom.

The reaction is carried out in particular in the presence of an alkali metal (preferably sodium), amide, phenolate or thiolate, in a solvent such as a ketone (for example, acetone), or an amide (for example, dimethylformamide), at a temperature ranging from 20 to 45° C.

The brominated derivative of formula (II) in which R" is a hydrogen atom is described in J. Org. Chem., 57, 2689 (1992), the disclosure of which is specifically incorporated herein by reference. The corresponding derivative in which R" is a hydroxyl radical can be prepared by analogy.

According to the present invention, the compounds of formula (I) in which R' is a radical of formula (Id) can be obtained from a mixed anhydride of the acid of formula (V):

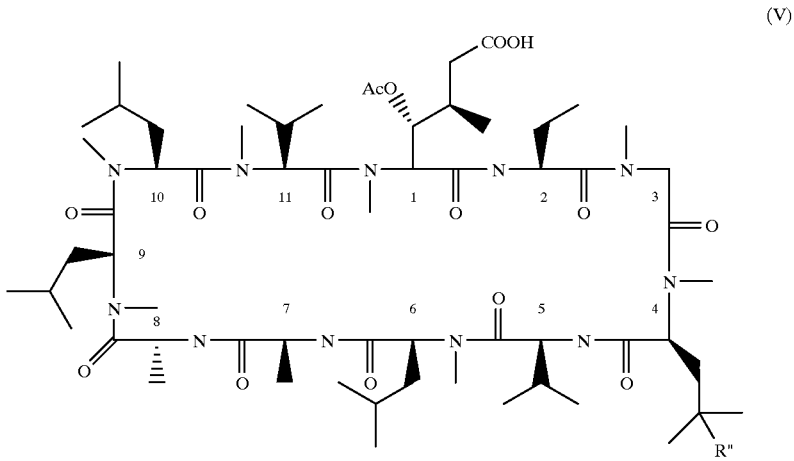

in which R" is defined as above and Ac represents an acetyl radical, first converted to the thiohydroxamic ester by reaction with a salt of N-hydroxy-2-thiopyridine with the exclusion of light, then photochemically converted, by irradiation, in the presence of a disulphide of formula (IV):

in which R'$_4$ is defined as above, and freed from the protective acetyl radical of the hydroxyl at the 3'-position and finally followed, if appropriate, by the subsequent operation of hydroxylation at the 4'-position of the [MeLeu]$^4$ residue, when it is desired to obtain a derivative in which R" is hydroxyl and when the reaction has been carried out starting from a cyclosporin derivative in which R" is a hydrogen atom, and/or followed by the subsequent operation of substitution of the chain of formula (Ia), when it is desired to obtain a cyclosporin derivative in which R is other than the hydrogen atom.

The reaction is carried out by analogy with the method described by D. Barton in Tetrahedron, 43, 4297 (1987), in an organic solvent such as a chlorinated solvent (chloroform, dichloromethane or dichloroethane, for example) or an ether (tetrahydrofuran or dioxane, for example), at a temperature ranging from 5 to 10° C. in darkness and then by irradiating with light at a temperature ranging from 10 to 30° C. Use is preferably made of the sodium salt of N-hydroxy-2-thiopyridine.

The acid of formula (V), the hydroxyl functional group of which is protected, was described by P. Paprika et al., Bioconjugate Chem., 3, 32–36 (1992).

The hydroxylation at the 4'-position of the [MeLeu]$^4$ residue to a 4'-hydroxy-MeLeu derivative is carried out according to or by analogy with the method described in European Patent Application EP 484,281, the disclosure of which is specifically incorporated herein by reference.

The substitution of the chain of formula (Ia) at the 3-position is carried out by reaction of a disulphide of formula (VI):

in which each R° and Alk are independently defined as above and in which, if appropriate, the functional groups which can interfere with the reaction have been protected beforehand, with an activated form of a cyclosporin derivative of formula (VII):

in which R' and R" are defined as above, followed by the removal, if appropriate, of the protective radical(s).

Activated form of the cyclosporin of formula (II) is understood to mean a form activated on the sarcosine at the 3-position. This activated form is preferably prepared in situ. The activation is generally carried out under an inert atmosphere by treatment with an organometallic derivative (in particular a lithium derivative, such as n-butyllithium, lithium diisopropylamide or a mixture, for example). It is also possible to prepare the activated form of the cyclosporin of formula (VII) in liquid ammonia in the presence of an alkali metal (sodium or lithium, for example) amide, at a temperature ranging from –32 to –38° C., in an ether (in particular tetrahydrofuran, t-butyl ethyl ether or a mixture).

The addition of the disulphide of formula (VI) is advantageously carried out in an organic solvent, such as a hydrocarbon (for example hexane) or an ether (diethyl ether, tetrahydrofuran or t-butyl methyl ether, for example), at a temperature ranging from –78 to 0° C. It is sometimes preferable to operate under nitrogen.

When the substituents of the R° radical can interfere with the reaction, it is preferable to protect them beforehand by radicals which are compatible and which can be put in place and removed without affecting the remainder of the molecule. Moreover, the hydroxyl radicals present on the cyclosporin can optionally be protected by any group which does not interfere with the reaction.

By way of example, the protective groups can be chosen from the radicals described by T. W. Greene, Protective Groups in Organic Synthesis, J. Wiley-Interscience Publication (1991) or by McOmie, Protective Groups in Organic Chemistry, Plenum Press (1973), the disclosure of which is specifically incorporated by reference herein.

When R" is a hydroxyl radical, the derivative of formula (VII) can be prepared as described in European Patent Application EP 484,281, the disclosure of which is specifically incorporated herein by reference, and then modification of the chain at the 1-position as described above.

The novel cyclosporin derivatives of formula (I) can be purified, if appropriate, by physical methods, such as crystallization or chromatography.

The cyclosporin derivatives according to the invention in which R° is carboxyl can be converted into metal salts or into addition salts with a nitrogenous base according to methods known per se. These salts can be obtained by the action of a metal base (for example, alkali metal or alkaline earth metal base), of ammonia or of an amine on a product according to the invention, in an appropriate solvent, such as

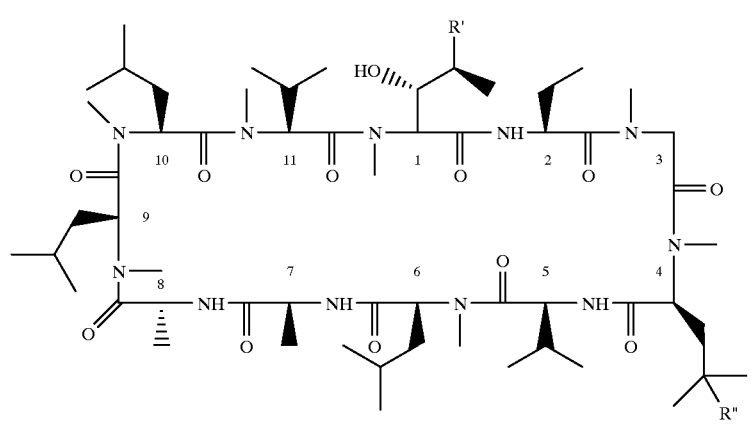

water or an alcohol. The salt formed precipitates after optional concentration of the solution; it is separated by filtration.

Mention may be made, as examples of pharmaceutically acceptable salts, of the salts with alkali metals (sodium, potassium or lithium) or with alkaline earth metals (magnesium or calcium), the ammonium salt or the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine).

The cyclosporin derivatives according to the invention in which $R°$ is $NR_1R_2$ can be converted into addition salts with acids by the known methods. It is understood that these salts also come within the scope of the present invention.

Mention may be made, as examples of addition salts with pharmaceutically acceptable acids, of the salts formed with inorganic acids (hydrochlorides, hydrobromides, sulphates, nitrates or phosphates) or with organic acids (succinates, fumarates, tartrates, acetates, propionates, maleates, citrates, methanesulphonates, p-toluenesulphonates or isethionates or with substitution derivatives of these compounds).

The novel cyclosporin derivatives according to the present invention can be particularly useful in the prophylaxis and treatment of retrovirus diseases and more particularly of AIDS and of syndromes associated with AIDS. Prophylaxis is understood to mean in particular the treatment of subjects who have been exposed to HIV viruses, in particular asymptomatic seropositives who present the risk of developing the disease in the months or years to come after the primary infection.

The products according to the invention can display an anti-retrovirus activity at concentrations devoid of any cytotoxic or cytostatic effect.

The activity of the products of formula (I) has been demonstrated in the techniques described by Pauwells et al., J. Virol. Meth., 20, 309 (1988) and by O. Schwatz et al., AIDS Research and Human Retroviruses, 4(6), 441–48 and cited by J. F. Mayaux et al., Proc. Nat. Acad. Sci. USA, 91, 3564–68 (1994). The inhibition of the cytopathogenic effect of the virus by the products according to the invention is exerted at values ranging from 2 to 25, expressed by the ratio of the $EC_{50}$ of cyclosporin A to the $EC_{50}$ of the product studied.

Particularly preferred products of formula (I) are those in which:

R is a hydrogen atom or a radical of structure (Ia) in which
Alk—$R°$ represents a methyl radical, or alternatively
Alk represents a straight- or branched-chain alkylene radical containing 2 to 6 carbon atoms and $R°$ represents an —$NR_1R_2$ radical in which $R_1$ and $R_2$, which are identical or different, represent alkyl radicals,
R' represents a (Ic) or (Id) radical

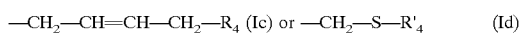

in which $R_4$ represents an alkylthio radical and $R'_4$ represents an alkyl radical, and R" represents a hydrogen atom or a hydroxyl radical, it being understood that the alkyl portions or radicals defined above are straight or branched and contain 1 to 4 carbon atoms, and with the proviso that R and R" are not simultaneously a hydrogen atom, and their pharmaceutically acceptable salts, when they exist.

According to an even more preferred embodiment, the invention relates to the cyclosporin derivatives of formula (I) in which:

R is a radical of structure (Ia) in which
Alk—$R°$ represents a methyl radical, or alternatively
Alk represents an ethylene radical and $R°$ represents an —$NR_1R_2$ radical in which $R_1$ and $R_2$, which are identical or different, represent alkyl radicals containing 1 or 2 carbon atoms,
R' represents a (Ic) or (Id) radical

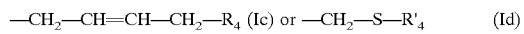

in which $R_4$ represents a methylthio radical and $R'_4$ represents a methyl radical, and R" represents a hydrogen atom or a hydroxyl radical, or alternatively R is a hydrogen atom, R' is defined as above and R" is a hydroxyl radical, and their pharmaceutically acceptable salts, when they exist, and, among these products, in particular the cyclosporin derivatives hereinbelow:

[(3 R,4 R)-3-hydroxy-5-methylthio-N-methyl-L-leucine]$^1$[(2 R)-methylthiosarcosine]$^3$-cyclosporin A;

[(3 R,4 R)-3-hydroxy-5-methylthio-N-methyl-L-leucine]$^1$[(2 R)-2'-(diethylamino)ethylthiosarcosine]$^3$-cyclosporin A;

[(3 R,4 R)-3-hydroxy-5-methylthio-N-methyl-L-leucine]$^1$ [4-hydroxy-N-methylleucine]$^4$-cyclosporin A;

[(4 R)-4-((E)-4-(methylthio)buten-2-yl)-N,4-dimethylthreonine]$^1$[(2 R)-2'-(diethylamino) ethylthiosarcosine]$^3$-cyclosporin A;

[(3 R,4 R)-3-hydroxy-5-methylthio-N-methyl-L-leucine]$^1$[(2 R)-2'-(dimethylamino)ethylthiosarcosine]$^3$[4'-hydroxy-N-methyl-L-leucine]$^4$-cyclosporin A;

and their pharmaceutically acceptable salts, when they exist.

The following examples, given without implied limitation, illustrate the present invention.

EXAMPLE 1

[(3 R,4 R)-3-Hydroxy-5-methylthio-N-methyl-L-leucine]$^1$[(2 R)-methylthiosarcosine]$^3$-cyclosporin A was prepared according to the following method: 14.8 cm$^3$ of a 1.6 M solution of n-butyllithium in hexane were added over 15 minutes, while maintaining the temperature at −70° C., to a solution, cooled to a temperature in the region of −70° C. and under nitrogen, of 3.3 cm$^3$ of diisopropylamine (distilled beforehand over calcium hydride) and of 16.6 cm$^3$ of 1,3-dimethyl-(1 H)-3,4,5,6-tetrahydropyrimidin-2-one in 33 cm$^3$ of tetrahydrofuran (distilled beforehand over sodium). The mixture was stirred at 0° C. for 20 minutes and then cooled to a temperature in the region of −78° C. A solution of 1.9 g of [(3 R,4 R)-3-hydroxy-5-methylthio-N-methyl-L-leucine]$^1$-cyclosporin A and of 14.4 cm$^3$ of 1,3-dimethyl-(1 H)-3,4,5,6-tetrahydropyrimidin-2-one in 27 cm$^3$ of tetrahydrofuran, cooled beforehand to a temperature in the region of −78° C., was added to the solution thus obtained while maintaining the temperature at approximately −68° C. The resulting mixture was stirred at a temperature in the region of −70° C. for 20 minutes and then 2.8 cm$^3$ of dimethyl disulphide were added over 5 minutes while maintaining the temperature at approximately −70° C. The mixture was stirred at a temperature in the region of −78° C. for 2 hours and then at 0° C. for 20 hours. 70 cm$^3$ of a 1 N hydrochloric acid solution and then 100 cm$^3$ of diethyl ether were slowly poured onto the reaction mixture. The organic phase was separated by settling, washed with a total of 100 cm³ of distilled water, dried over sodium sulphate, filtered and concentrated under reduced pressure (2.7 kPa) at a temperature in the region of 40° C. The solid obtained (2.1 g) was purified by chromatography on a silica column (0.04–0.063 mm), elution being carried out with ethyl acetate. The fractions containing the expected product were combined and concentrated under reduced pressure (2.7 kPa) at a temperature in the region of 40° C. and gave a solid which was triturated from 20 cm³ of pentane. After filtration, 110 mg of [(3 R,4 R)-3-hydroxy-5-methylthio-N-methyl-L-leucine]¹[(2 R)-methylthio-sarcosine]³-cyclosporin A were obtained in the form of a white solid that melted at approximately 150° C.

¹H N.M.R. spectrum (400 MHz, CDCl₃, δ in ppm): 1.27 (d, J=7 Hz, 3 H, 8β CH₃), 1.36 (d, J=7.5 Hz, 3 H, 7β CH₃), 2.04 (s, 3 H, 1ε SCH₃), 2.15 (s, 3 H, 3β SCH₃), 2.30 and 2.83 (2 dd, respectively J=13 and 8.5 Hz and J=13 and 3.5 Hz, each 1 H, 1δ CH₂S), 2.44 (mt, 1 H, 5β CH), 2.70, 2.72, 3.11, 3.28, 3.44 and 3.53 (6 s, respectively 3 H, 3 H, 6 H, 3 H, 3 H and 3 H, 7 NCH₃), 3.84 (mt, 1 H, 1β CH), 4.02 (d, J=6 Hz, 1 H, OH at 1β), 4.55 (mt, 1 H, 7α CH), 4.66 (t, J=9 Hz, 1 H, 5α CH), 4.84 (mt, 1 H, 8α CH), 4.96 (dd, J=9.5 and 6 Hz, 1 H, α CH of a leucine), from 5.00 to 5.15 (mt, 2 H, 2α CH and α CH of a leucine), 5.17 (d, J=11 Hz, 1 H, 11α CH), 5.28 (dd, J=12 and 4 Hz, 1 H, α CH of a leucine), 5.49 (d, J=6 Hz, 1 H, 1α CH), 5.72 (dd, J=11 and 4 Hz, 1 H, α CH of a leucine), 5.78 (s, 1 H, 3α CH), 7.17 (d, J=8 Hz, 1 H, CONH at 8), 7.34 (d, J=9 Hz, 1 H, CONH at 5), 7.66 (d, J=7.5 Hz,1 H, CONH at 7), 7.93 (d, J=10 Hz, 1 H, CONH at 2).

[(3 R,4 R)-3-Acetyloxy-5-methylthio-N-methyl-L-leucine]¹ -cyclosporin A was prepared with the exclusion of light and under an inert atmosphere according to the following method:

1.2 cm³ of N-methylmorpholine (distilled beforehand) and 1.4 Cm³ of isobutyl chloroformate (distilled beforehand) were added successively, over 5 min and 10 min respectively, to a solution, cooled to a temperature in the region of −15° C., of 12.5 g of [(3 R,4 R)-3-acetyloxy-5-carboxy-N-methyl-L-leucine]¹-cyclosporin A in 100 cm³ of 1,2-dichloroethane. The reaction mixture was stirred for 90 min at a temperature in the region of −15° C. and then a solution of 1.5 g of sodium salt of the oxide of 2-mercaptopyridine and of 1.7 cm³ of triethylamine in 25 cm³ of 1,2-dichloroethane was added over 10 minutes. The reaction mixture was stirred with the exclusion of light for 17 hours at a temperature in the region of −20° C. 8.9 cm³ of dimethyl disulphide (distilled beforehand) were subsequently added over 5 min and then the reaction mixture was irradiated for 3 hours using two 60 W tungsten lamps while maintaining the temperature between 0 and 10° C. The resulting mixture was then concentrated under reduced pressure (2.7 kPa) at a temperature in the region of 40° C. The residue was taken up in 200 cm³ of diethyl ether, 100 cm³ of distilled water and 20 cm³ of an N hydrochloric acid solution. The organic phase was separated by settling and then washed successively with a total of 150 cm³ of distilled water and 25 cm³ of a molar aqueous ethanolamine solution and then with a total of 125 cm³ of distilled water. The organic phase was dried over magnesium sulphate, filtered and concentrated under reduced pressure (2.7 kPa) at a temperature in the region of 40° C. The yellow foam obtained (10.5 g) was purified by chromatography on a silica column (0.04–0.063 mm), elution being carried out with ethyl acetate. The fractions containing the expected product were combined and concentrated under reduced pressure (2.7 kPa) at a temperature in the region of 40° C. and gave 4.0 g of [(3 R,4 R)-3-acetyloxy-5-methylthio-N-methyl-L-leucine]¹-cyclosporin A in the form of a white foam (R_f= 0.31; silica thin layer chromatography; eluent: ethyl acetate).

¹H N.M.R. spectrum (400 MHz, CDCl₃, δ in ppm): 1.28 (d, J=7 Hz, 3 H, 8β CH₃), 1.32 (d, J=7.5 Hz, 3 H, 7β CH₃), 1.92 (s, 3 H, COCH₃ at 1β), 2.00 (s, 3 H, 1ε SCH₃), 2.34 and 2.50 (2 dd, respectively J=13 and 5 Hz and J=13 and 7 Hz, each 1 H, 1δ SCH₂), 2.45 (mt, 1 H, 5β CH), 2.65, 2.68, 3.05, 3.20, 3.26, 3.29 and 3.45 (7 s, each 3 H, 7 NCH₃), 3.14 and 4.66 (2 d, J=14 Hz, each 1 H, 3α CH₂), 4.42 (mt, 1 H, 7α CH), 4.75 (t, J=9.5 Hz, 1 H, 5α CH), 4.86 (mt, 1 H, 8α CH), 4.96 (mt, 1 H, 2α CH), 5.00 (d, J=11 Hz, 1 H, 11α CH), 5.12 (dd, J=7 and 5 Hz, 1 H, α CH of a leucine), 5.35 (dd, J=12 and 4 Hz, 1 H, α CH of a leucine), from 5.40 to 5.60 (mt, 3 H, α CH of a leucine, 1α CH and 1β CH), 5.68 (dd, J=11 and 4 Hz,1 H, α CH of a leucine), 7.51 (d, J=8 Hz,1 H, CONH at 8), 7.61 (d, J=9.5 Hz, 1 H, CONH at 5), 8.07 (d, J=7.5 Hz, 1 H, CONH at 7), 8.53 (d, J=10 Hz, 1 H, CONH at 2).

[(3 R,4 R)-3-Acetyloxy-5-carboxy-N-methyl-L-leucine]¹-cyclosporin A was prepared according to P. Paprika et al., Bioconjugate Chem., 3, 32–36 (1992), the disclosure of which is specifically incorporated by reference herein.

[(3 R,4 R)-3-Hydroxy-5-methylthio-N-methyl-L-leucine]¹-cyclosporin A was prepared according to the following method:

7.2 cm³ of a 0.5 M sodium methoxide solution were added to a solution of 310 mg of guanidine hydrochloride in 20 cm³ of methanol. The solution obtained was added to a solution of 3.75 g of [(3 R,4 R)-3-acetyloxy-5-methylthio-N-methyl-L-leucine]¹-cyclosporin A in 130 cm³ of methanol. The resulting mixture was stirred at a temperature in the region of 20° C. for 48 hours and then the mixture was concentrated under reduced pressure (2.7 kPa) at a temperature in the region of 40° C. The residue was taken up in 100 cm³ of diethyl ether. The organic phase was washed with a total of 150 cm³ of distilled water, dried over sodium sulphate, filtered and concentrated under reduced pressure (2.7 kPa) at a temperature in the region of 40° C. The solid obtained (3.5 g) was purified by chromatography on a silica column (0.04–0.063 mm), elution being carried out with ethyl acetate. The fractions containing the expected product were combined and concentrated under reduced pressure (2.7 kPa) at a temperature in the region of 40° C. and gave 2.5 g of [(3 R,4 R)-3-hydroxy-5-methylthio-N-methyl-L-leucine]¹-cyclosporin A in the form of a white foam (R_f= 0.32; silica thin layer chromatography; eluent: ethyl acetate).

¹H N.M.R. spectrum (400 MHz, CDCl₃, δ in ppm): 1.26 (d, J=7 Hz, 3 H, 8β CH₃), 1.36 (d, J=7.5 Hz, 3 H, 7β CH₃), 1.90 (mt, 1 H, CH at 1γ), 2.04 (s, 3 H, 1ε SCH₃), 2.31 and 2.87 (2 dd, respectively J=13 and 9 Hz and J=13 and 3.5 Hz, each 1 H, 1δ CH₂S), 2.43 (mt, 1 H, 5β CH), 2.70, 2.72, 3.11, 3.26, 3.39 and 3.52 (6 s, respectively 3 H, 3 H, 6 H, 3 H, 3 H and 3 H, 7 NCH₃), 3.20 and 4.74 (2 d, J=14.5 Hz, each 1 H, 3α CH₂), 3.85 (mt, 1 H, 1β CH), 4.21 (d, J=6 Hz, 1 H, OH at 1β), 4.54 (mt, 1 H, 7α CH), 4.65 (t, J=9 Hz, 1 H, 5α CH), 4.83 (mt, 1 H, 8α CH), 4.97 (dd, J=9.5 and 6 Hz, 1 H, α CH of a leucine), from 5.00 to 5.15 (mt, 2 H, 2α CH and α CH of a leucine), 5.16 (d, J=11 Hz, 1 H, 11α CH), 5.34 (dd, J12 and 4 Hz, 1 H, α CH of a leucine), 5.48 (d, J=6 Hz, 1 H, 1α CH), 5.72 (dd, J=11 and 4 Hz, 1 H, α CH of a leucine), 7.17 (d, J=8 Hz, 1 H, CONH at 8), 7.48 (d, J=9 Hz, 1 H, CONH at 5), 7.67 (d, J=7.5 Hz, 1 H, CONH at 7), 7.97 (d, J=10 Hz, 1 H, CONH at 2).

EXAMPLE 2

[(3 R,4 R)-3-Hydroxy-5-methylthio-N-methyl-L-leucine]¹[(2 R)-2'-(diethylamino)ethylthiosarcosine]³- cyclosporin A was prepared by carrying out the preparation as in Example 1 but from 1.1 g of [(3 R,4 R)-3-hydroxy-5-methylthio-N-methyl-L-leucine]$^1$-cyclosporin A and 5.2 g of 2-(diethylamino)ethyl disulphide and by then purifying as described hereinbelow.

The organic phase was separated by settling, washed with a total of 90 cm$^3$ of distilled water, dried over sodium sulphate, filtered and concentrated under reduced pressure (2.7 kPa) at a temperature in the region of 40° C. The oily residue obtained (6.2 g) was triturated with 150 cm$^3$ of pentane to result in 700 mg of a white solid which was purified by chromatography on a silica column (0.04–0.063 mm), elution being carried out with a mixture of ethyl acetate and methanol (4/1 by volume). The fractiorld; containing the expected product were combined and concentrated under reduced pressure (2.7 kPa) at a temperature in the region of 40° C. and gave 300 mg of a white solid which was purified by a second chromatographic purification on a silica column (0.04–0.063 mm), elution being carried out with a mixture of ethyl acetate, 1-butanol, ethanol and water (8/6/3/3 by volume). The fractions containing the expected product were combined and concentrated under reduced pressure (2.7 kPa) at a temperature in the region of 40° C. and gave 150 mg of a white solid which was triturated with 5 cm$^3$ of pentane. After filtration, 33 mg of [(3 R,4 R)-3-hydroxy-5-methylthio-N-methyl-L-leucine]$^1$[(2 R)-2'-(diethylamino)ethylthiosarcosine]$^3$-cyclosporin A were obtained in the form of a white solid that melted at approximately 140° C.

$^1$H N.M.R. spectrum (400 MHz, CDCl$_3$, δ in ppm). Two conformers are observed in the proportions 75% and 25%. 1.37 (d, J=7.5 Hz, 3 H, 7β CH$_3$), 2.00 and 2.03 (s, a total of 3 H, 1δ SCH$_3$), from 2.30 to 2.90 (mt, the 11 H corresponding to the SCH$_2$CH$_2$N(CH$_3$)$_2$ of the 2-(diethylamino) ethylthio at 3α, 1δ SCH$_2$ and 5β CH), 3.80 (mt, 1 H, 1β CH), 3.97 (broad d, J=6 Hz,1 H, OH at 1β), 4.54 and from 4.59 to 4.70 (2 mts, a total of 1 H, 7α CH), from 4.60 to 4.70 (mt, 1 H, 5α CH), 4.84 (mt, 1 H, 8α CH), from 4.85 to 5.45 (mt, 4 H,11α CH and α CH of three leucines), 5.49 and 5.66 (2 d, respectively J=6 and J=9 Hz, a total of 1 H,1α CH), 5.72 (dd, J=10.5 and 4 Hz,1 H, α CH of a leucine), 5.79 and 5.98 (2 s, a total of 1 H, 3α CH), 7.05 and 7.17 (2 d, J=8 Hz, a total of 1 H, CONH at 8), 7.32 and 7.35 (2 d, J=9 Hz, a total of 1 H, CONH at 5), 7.42 and 7.76 (2 d, J=7.5 Hz, a total of 1 H, CONH at 7), 7.94 (broad d, J=10 Hz,1 H, CONH at 2).

EXAMPLE 3

[(3 R,4 R)-3-Hydroxy-5-methylthio-N-methyl-L-leucine]$^1$[4-hydroxy-N-methylleucine]$^4$-cyclosporin A was prepared by hydroxylation, with the Sebekia benihana strain, of the product as obtained in Example 1, on which the chain at the 1-position had been initially modified.

Two 250 cm$^3$ Erlenmeyer flasks, containing 50 cm$^3$ of medium A (peptone: 10 g; yeast extract: 5 g; starch: 10 g; glucose: 5 g; agar: 1 g; water: q.s. for 1000 cm$^3$; pH adjusted to 7.2; sterilization at 121° C. for 25 minutes), were inoculated at 2% from two frozen liquid phials of the Sebekia benihana strain and were then incubated with agitation at 220 revolutions/minute for 72 hours at a temperature in the region of 28° C. These four Erlenmeyer flasks constituted the inoculum Erlenmeyer flasks.

Seven 250 cm$^3$ Erlenmeyer flasks containing 50 cm$^3$ of medium B (glucose: 10 g; soluble starch: 10 g; yeast extract: 2.5 g; soya flour: 12.5 g; dextrin: 10 g; potassium dihydrogenphosphate: 0.12 g; magnesium sulphate heptahydrate: 0.10 g; dipotassiuni hydrogenphosphate: 0.25 g; calcium chloride dihydrate: 0.05 g; [1 cm$^3$ of a solution containing H$_3$BO$_3$:0.1 g; FeSO$_4$7 H$_2$O: 5 g; Kl: 0.05 g; CaCl$_2$.6 H$_2$O: 2 g; CuSO$_4$.5 H$_2$O: 0.2 g; MnCl$_2$.4 H$_2$O: 2 g; ZnSO$_4$.7 H$_2$O: 4 g; (NH$_4$)$_2$Mo$_7$O$_{24}$: 0.2 g; 97% H$_2$SO$_4$: 1 cm$^3$; H$_2$O: q.s. for 1000 cm$^3$]; water: q.s. for 1000 cm$^3$; pH adjusted to 7.2–7.5; sterilization at 121 ° C. for 25 minutes) were inoculated at 4% from the inoculum Erlenmeyer flasks and were then incubated with agitation at 220 revolutions/minute for 48 hours at a temperature in the region of 28° C. before addition of [(3 R,4 R)-3-hydroxy-5-methylthio-N-methyl-L-leucine]$^1$-cyclosporin A. These Erlenmeyer flasks constituted the production Erlenmeyer flasks.

A solution of 105 mg of [(3 R,4 R)-3-hydroxy-5-methylthio-N-methyl-L-leucine]$^1$-cyclosporin A in 3.5 cm$^3$ of ethanol was prepared at the time of use and then filtered through a 0.2 μm Millipore filter. 0.5 cm$^3$ of the [(3 R,4 R)-3-hydroxy-5-methylthio-N-methyl-L-leucine]$^1$[4-hydroxy-N-methylleucine]$^4$-cyclosporin A mother solution was added under sterile conditions to each of the production Erlenmeyer flasks. The Erlenmeyer flasks were incubated with agitation at 220 revolutions/minute at a temperature in the region of 28° C. After 72 hours, each Erlenmeyer flask was extracted with a mixture of acetonitrile, n-heptane and methyl t-butyl ether (2/1/1 by volume). The intermediate organic phases were combined, concentrated under reduced pressure (2.7 kPa) at a temperature in the region of 40° C. and then taken up again in 10 cm$^3$ of methanol. 5 g of Sorbsil C60 silica (40–60 μm) (Prolabo) were added to the solution obtained and the combined mixture was concentrated under vacuum (2.7 kPa) and then dried for 2 hours in an oven at a temperature in the region of 25° C. The residue was chromatographed on Sorbsil C60 silica (40–60 μm) (Prolabo) eluted with 1,2-dichloroethane (throughput 20 cm$^3$/hour, 10-cm$^3$ fractions). Starting with fraction 8, elution was carried out with a mixture of 1,2-dichloroethane and methanol (99/1 by volume) until fraction 15. From this fraction on, the 1,2-dichloroethane/methanol (49/1 by volume) elution system was used. The fractions containing only the expected product were combined and concentrated to dryness under reduced pressure (2.7 kPa) at a temperature in the region of 40° C. The residue was taken up again in 2 cm$^3$ of ethyl acetate and 1 cm$^3$ of cyclohexane and was then left for 3 hours at a temperature in the region of 4° C. The solid was subsequently filtered off and washed with heptane to result in 33 mg of [(3 R,4 R)-3-hydroxy-5-methylthio-N-methyl-L-leucine]$^1$[4-hydroxy-N-methylleucine]$^4$-cyclosporin A in the form of a white solid.

$^1$H N.M.R. spectrum (400 MHz, CDCl$_3$, δ in ppm): 1.36 (d, J=7.5 Hz, 3 H, 7δ CH$_3$), 2.04 (s, 3 H, 1ε SCH$_3$), 2.08 and 2.37 (2 mts, the 2 H corresponding to the 4β CH$_2$), 2.40 and 2.83 (respectively mt and dd, J=13 and 3.5 Hz, each 1 H, 1δ CH$_2$S), 2.44 (mt,1 H, 5β CH), 2.70 and 2.72 (2 s, each 3 H, 2 NCH$_3$), 3.18 and 4.70 (2 d, J=14 Hz, each 1 H, 3α CH$_2$), 3.86 (mt, 1 H, 1β CH), 4.52 (mt, 1 H, 7α CH), 4.68 (t, J=9 Hz,1 H, 5α CH), 4.84 (mt, 1 H, 8α CH), from 4.95 to 5.20 (mt, 3 H, 2α CH and α CH of two leucines), 5.16 (d, J=11 Hz, 1 H, 11α CH); 5.43 (d, J=6 Hz, 1 H, 1α CH), 5.58 (mt, 1 H, 4α CH), 5.72 (dd, J=11 and 4 Hz, 1 H, α CH of a leucine), 7.22 (d, J=8 Hz, 1 H, CONH at 8), 7.68 (d, J=9 Hz, 1 H, CONH at 5), 7.73 (d, J=7.5 Hz, 1 H, CONH at 7), 8.06 (d, J=10 Hz, 1 H, CONH at 2).

EXAMPLE 4

[(4 R)-4-((E)-4-(Methylthio)buten-2-yl)-N,4-dimethylthreonine]$^1$[(2 R)-methylthiosarcosine]$^3$-cyclosporin A:

A solution of 1 g of [(4 R)-4-((E)-4-(methylthio)buten-2-yl)-N,4-dimethylthreonine]$^1$-cyclosporin A in 40 cm$^3$ of tetrahydrofuran (THF) and 1.44 cm³ of 1,3-dimethyl-(1 H)-3,4,5,6-tetrahydropyrimidin-2-one (DMPU) was added dropwise at −70° C. to 6 cm³ of a 2 N solution of lithium diisopropylamide (LDA) in THF/heptane under an argon atmosphere. The temperature of the solution, dark orange in color, was raised to −30° C. and thus maintained for 30 minutes. The mixture was subsequently cooled to −70° C. and 1.40 cm³ of dimethyl disulphide were added dropwise. After 1 hour, the temperature was raised to −10° C. and thus maintained for 2 hours. The reaction was halted by the addition of 1 N hydrochloride acid (1 N HCl) until neutrality and the mixture was extracted three times with 30 cm³ of ethyl ether. The combined organic phases were washed twice with 20 cm³ of water and 20 cm³ of a saturated NaCl solution, then dried over anhydrous sodium sulphate, filtered and concentrated to dryness under reduced pressure (2.7 kPa) at a temperature in the region of 40° C. An orange oil was thus obtained which was purified by chromatography on a silica column (0.04–0.063 mm), elution being carried out with the 8/2 ethyl acetate/dichloromethane mixture. The fractions containing the expected product were combined and concentrated under reduced pressure (2.7 kPa) at a temperature in the region of 40° C. and gave 81 mg of [(4 R)-4-((E)-4-(methylthio)buten-2-yl)-N,4-dimethylthreonine]$^1$[(2 R)-methylthiosarcosine]$^3$-cyclosporin A in the form of a white solid which melted at approximately 130° C.

$^1$H N.M.R. spectrum (400 MHz, CDCl$_3$, δ in ppm): 1.28 (d, J=7 Hz, 3 H, 8β CH$_3$), 1.35 (d, J=7.5 Hz, 3 H, 7β CH$_3$), 1.99 (s, 3 H, SCH$_3$ of the chain at 1), 2.15 (s, 3 H, 3β SCH$_3$), 2.45 (mt, 1 H, 5β CH), 2.69, 2.71, 3.12, 3.27, 3.45 and 3.52 (6 s, respectively 3 H, 3 H, 6 H, 3 H, 3 H and 3 H, 7 NCH$_3$), 3.05 (d, J=7.5 Hz, 2 H, SCH$_2$ of the chain at 1), 3.5:3 (broad d, J=6 Hz,1 H, 1β OH), 3.78 (mt, 1 H,1β CH), 4.55 (mt,1 H, 7α CH), 4.67 (t, J=9 Hz, 1 H, 5α CH), 4.85 (mt, 1 H, 8α CH), 4.97 (dd, J=9 and 6 Hz,1 H, α CH of a leucine), from 5.00 to 5.10 (mt, 3 H, 2α CH, α CH of a leucine and 11α CH), 5.23 (dd, J=12 and 4 Hz, 1 H, α CH of a leucine), from 5.25 to 5.50 (mt, 2 H, CH=CH), 5.52 (d, J=6 Hz, 1 H, 1α CH), 5.72 (dd, J=11 and 4 Hz, 1 H, α CH of a leucine), 5.78 (s, 1 H, 3α CH), 7.17 (d, J=8 Hz, 1 H, CONH at 8), 7.37 (d, J=9 Hz, 1 H, CONH at 5), 7.21 (d, J=7.5 Hz,1 H, CONH at 7), 8.02 (d, J=10 Hz,1 H, CONH at 2).

[(4 R)-4-((E)-4-(Methylthio)buten-2-yl)-N,4-dimethylthreonine]$^1$-cyclosporin A was prepared according to the following method:

0.35 g of [(4 R)-4-((E)-4-(methylthio)buten-2-yl)-O-acetyl-N,4-dimethylthreonine]$^1$-cyclosporin A in 5 cm³ of methanol was added, at 20° C. under argon, to a sodium methoxide solution (prepared beforehand with 7 mg of sodium metal in 1 cm³ of methanol). The yellow mixture was left stirring for 24 hours, then acidified to pH 6 by the addition of acetic acid and concentrated to dryness. The residue was triturated in ethyl ether and filtered to give a beige solid which was purified by chromatography on a silica column (0.04–0.063 mm), elution being carried out with ethyl acetate saturated with water. The fractions containing the expected product were combined and concentrated under reduced pressure (2.7 kPa) at a temperature in the region of 40° C. and gave 100 mg of [(4 R)-4-((E)-4-(methylthio)buten-2-yl)-N,4-dimethylthreonine]$^1$-cyclosporin A in the form of a white solid which melted at approximately 148° C.

$^1$H N.M.R. spectrum (400 MHz, CDCl$_3$, δ in ppm): 1.27 (d, J=7 Hz, 3 H, 8α CH$_3$), 1.35 (d, J=7.5 Hz, 3 H, 7β CH$_3$), 1.99 (s, 3 H, SCH$_3$ of the chain at 1), 2.44 (mt,1 H, 5β CH), 2.70, 2.72, 3.12, 3.27, 3.30 and 3.52 (6 s, respectively 3 H, 3 H, 6 H, 3 H, 3 H and 3 H, 7 NCH$_3$), 3.06 (d, J=7.5 Hz, 2 H, SCH$_2$ of the chain at 1), 3.20 and 4.73 (2 d, J=14.5 Hz, each 1 H, 3α CH$_2$), 3.72 (d, J=6 Hz, 1 H, OH at 1β), 3.81 (mt, 1 H, CH at 1β), 4.54 (mt, 1 H, 7α CH), 4.66 (t, J=9 Hz, 1 H, 5α CH), 4.84 (mt, 1 H, 8α CH), from 4.90 to 5.10 (mt, 3 H, 2α CH and α CH of two leucines), 5.10 (d, J=11 Hz, 1 H, 11α CH), from 5.25 to 5.50 (mt, 3 H, α CH of a leucine and CH=CH), 5.51 (d, J=6 Hz, 1 H, 1α CH), 5.71 (dd, J=11 and 4 Hz, 1 H, α CH of a leucine), 7.17 (d, J=8 Hz, 1 H, CONH at 8), 7.50 (d, J=9 Hz, 1 H, CONH at 5), 7.71 (d, J=7.5 Hz, 1 H, CONH at 7), 8.09 (d, J=10 Hz, 1 H, CONH at 2).

[(4 R)-4-((E)-4-(Methylthio)buten-2-yl)-O-acetyl-N,4-dimethylthreonine]$^1$-cyclosporin A was prepared according to the following method:

23 mg of sodium methanethiolate were added, at 20° C. under argon, to a solution of 0.4 g of [(4 R)-4-((E)-4-bromobuten-2-yl)-O-acetyl-N,4-dimethylthreonine]$^1$-cyclosporin A in 7 cm³ of dimethylformamide (DMF). The yellow mixture was left stirring for 24 hours and then 10 cm³ of water were added to obtain a white precipitate which was filtered off and dried. 0.37 g of [(4 R)-4-((E)-4-(methylthio)buten-2-yl)-O-acetyl-N,4-dimethylthreonine]$^1$-cyclosporin A was thus obtained in the form of a white solid which melted at approximately 137° C., and was subsequently used.

$^1$H N.M.R. spectrum (400 MHz, CDCl$_3$, δ in ppm): 1.28 (d, J=7 Hz, 3 H, 8β CH$_3$), 1.33 (d, J=7.5 Hz, 3 H, 70 CH$_3$), 1.98 (s, 3 H, SCH$_3$ of the chain at 1), 2.03 (s, 3 H, OCOCH$_3$ at 1β), 2.43 (mt,1 H, 5β CH), 2.66, 2.70, 3.11, 3.21, 3.25, 3.27 and 3.45 (7 s, each 3 H, 7 NCH$_3$), from 2.90 to 3.10 (mt, 2 H, SCH$_2$ of the chain at 1), 3.18 and 4.65 (2 d, J=14 Hz, each 1 H, 3α CH$_2$), 4.41 (mt, 1 H, 7α CH), 4.74 (t, J=9.5 Hz, 1 H, 5α CH), 4.85 (mt, 1 H, 8α CH), from 4.85 to 5.00 (mt, 2 H, 2α CH and 11α CH), 5.15 (dd, J=8 and 6 Hz,1 H, α CH of a leucine), from 5.15 to 5.40 (mt, 4 H, α CH of two leucines and CH=CH), 5.53 (s, 2 H, 1α CH and 1β CH), 5.69 (dd, J=11 and 4 Hz, 1 H, α CH of a leucine, 7.47 (d, J=8 Hz, 1 H, CONH at 8), 7.53 (d, J=9.5 Hz, 1 H, CONH at 5), 8.04 (d, J=7.5 Hz, 1 H, CONH at 7), 8.57 (d, J=10 Hz, 1 H, CONH at 2).

EXAMPLE 5

[(4 R)-4-((E)-4-(Methylthio)buten-2-yl)-N,4-dimethylthreonine]$^1$ [(2 R)-2'-(diethylamino) ethylthiosarcosine]$^3$-cyclosporin A was prepared, according to the method described in Example 4, from 1 g of [(4 R)-4-((E)4-(methylthio)buten-2-yl)-N,4-dimethylthreonine]$^1$-cyclosporin A by using 3 g of N,N-diethylaminoethanethiol disulphide. At the end of addition of the disulphide, the mixture was maintained at −70° C. for 1 hour and then for 16 hours at approximately −10° C. After reheating to 10° C., the mixture was acidified to pH 2 with 1 N HCl and extracted with 60 cm³ of ethyl ether and then the organic phase was extracted three times with 25 cm³ of 1 N Hcl. The aqueous phase was basified to pH =8 with sodium carbonate and extracted three times with 50 cm³ of ethyl ether. The combined organic phases were dried over anhydrous sodium sulphate, filtered and concentrated to dryness under reduced pressure (2.7 kPa) at a temperature in the region of 40° C. The thick orange oil obtained was filtered through a cake of silica (0.04–0.063 mm) with the 9/1 methanol/dichloromethane mixture and then, after combining the fractions containing the product and evaporating the solvent, the solid residue obtained was purified by chromatography on a silica column (0.04–0.063 mm), elution being carried out with the 4/3/1.5/0.5 ethyl acetate/butanol/ethanol/water mixture. The fractions containing the expected product were combined and concentrated under reduced pressure (2.7 kPa, at a temperature in the region of 40° C. and gave 37 mg of [(4 R)-4-((E)-4-(methylthio)buten-2-yl)-N,4-dimethylthreonine]$^1$[(2 R)-2'-(diethylamino)ethylthio-sarcosine]$^3$-cyclosporin A in the form of a white solid which melted at approximately 135° C.

$^1$H N.M.R. spectrum (400 MHz, CDCl$_3$, δ in ppm): 1.26 (d, J=7 Hz, 3 H, 8β CH$_3$), 1.35 (d, J=7.5 Hz, 3 H, 7β CH$_3$), 1.99 (s, 3 H, SCH$_3$ of the chain at 1), 2.46 (mt, 1 H, 5β CH), from 2.45 to 3.35 (mt, the 8 H corresponding to the SCH$_2$CH$_2$N(CH$_2$)$_2$ of the 2-diethylaminoethylthio at 3α), 3.04 (d, J=7.5 Hz,1 H, CH$_2$S of the chain at 1), 2.68, 2.72, 3.11, 3.13, 3.25, 3.44 and 3.51 (7 s, each 3 H, 7 NCH$_3$), 3.58 (broad d, J=6 Hz, 1 H, OH at 1β), 3.25 (mt, 1 H, 1β CH), 4.55 (mt, 1 H, 7α CH), 4.65 (t, J=9 Hz, 1 H, 5α CH), 4.84 (mt,1 H, 8α CH), 4.97 (dd, J=9 and 6 Hz,1 H, α CH of a leucine), from 5.00 to 5.15 (mt, 3 H, 2α CH, α CH of a leucine and 11α CH), 5.22 (dd, J=12 and 4 Hz, 1 H, α CH of a leucine), from 5.20 to 5.55 (mt, 2 H, CH=CH), 5.52 (d, J=6 Hz, 1 H, 1α CH), 5.72 (dd, J=10.5 and 4 Hz, 1 H, α CH of a leucine), 5.98 (s, 1 H, 3α CH), 7.17 (d, J=8 Hz, 1 H, CONH at 8), 7.36 (d, J=9 Hz,1 H, CONH at 5), 7.70 (d, J=7.5 Hz, 1 H, CONH at 7), 8.04 (d, J=10 Hz, 1 H, CONH at 2).

EXAMPLE 6

[(3 R,4 R)-3-Hydroxy-5-methylthio-N-methyl-L-leucine]$^1$[(2 R)-2'-(dimethylamino)ethylthiosarcosine]$^3$[4'-hydroxy-N-methyl-L-leucine]$^4$-cyclosporin A:

50 mg of sodium metal and then 10 mg of ferric nitrate were added to 70 cm$^3$ of ammonia maintained at a temperature in the region of −33° C. As soon as the blue coloration of the mixture had disappeared, 0.626 g of sodium metal were added over 15 minutes. The mixture was stirred at −33° C. for 90 minutes and then a solution of 2.4 g of [(3 R,4 R)-3-hydroxy-5-methylthio-N-methyl-L-leucine]$^1$[4'-hydroxy-N-methyl-L-leucine]$^4$-cyclosporin A in 80 cm$^3$ of tert-butyl methyl ether was added dropwise over a time of approximately 30 minutes, followed by a solution of 1.63 g of N,N-dimethylaminoethanethiol disulphide in 10 cm$^3$ of tert-butyl methyl ether. The reaction mixture was stirred at −33° C. for 30 minutes and then 2.35 g of ammonium chloride were added portionwise. The ammonia was allowed to evaporate with stirring, the temperature of the mixture changing from −32° C. to 20° C. over 12 hours. The reaction mixture was diluted with 100 cm$^3$ of diethyl ether and then filtered. The solid was washed with a total of 300 cm$^3$ of diethyl ether. The combined organic phases were concentrated under reduced pressure (2.7 kPa) at a temperature in the region of 30° C.

The residual oil was stirred for 48 hours at a temperature in the region of 20° C. with 200 cm$^3$ of pentane. The solid formed was filtered off and then washed with a total of 150 cm$^3$ of pentane. The solid was purified by chromatography on a silica column (0.020–0.045 mm) eluted with a 9/1 (by volume) mixture of ethyl acetate and methanol, and 50-cm$^3$ fractions were collected. The fractions containing the expected product were concentrated under reduced pressure (2.7 kPa) at a temperature in the region of 40° C. and gave 0.900 g of [(3 R,4 R)-3-hydroxy-5-methylthio-N-methyl-L-leucine]$^1$[(2 R)-2'-(dimethylamino)ethylthiosarcosine]$^3$[4'-hydroxy-N-methyl-L-leucine]$^4$-cyclosporin A in the form of a white solid which melted at a temperature in the region of 154° C.

$^1$H N.M.R. spectrum (400 MHz, CDCl$_3$, δ in ppm): 1.36 (d, J=7.5 Hz, 3 H, 7β CH$_3$), 2.04 (s, 3 H, 1ε CH$_3$), 2.25 (s, 6 H, N(CH$_3$)$_2$ of the 2-dimethylaminoethylthio at 3α), from 2.25 to 2.85 (mt, 7 H, the 7 H corresponding to the CH$_2$ at 1γ, NCH$_2$CH$_2$S of the 2-dimethylaminoethylthio at 3α and 1 H of the CH$_2$ at 4β), 2.70, 2.72, 3.13, 3.18, 3.28, 3.45 and 3.51 (7 s, each 3 H, the 7 NCH$_3$), 3.64 (d, J=6.5 Hz,1 H, OH at 1β), 3.86 (mt, H, 1β CH), 4.53 (mt, 1 H, 7α CH), 4.67 (t, J=9 Hz,1 H, 5α CH), 4.83 (mt, 1 H, 8α CH), from 4.95 to 5.15 (mt, 3 H, 2α CH and α CH of two leucines), 5.15 (d, J=11 Hz, 1 H, 11α CH), 5.42 (d, J=6.5 Hz, 1 H, 1α CH), 5.46 (t, J=6 Hz, 1 H, 4α CH), 5.71 (dd, J=11 and 4 Hz,1 H, α CH of a leucine), 6.00 (s, 1 H, 3α CH), 7.22 (d, J=8 Hz, 1 H, CONH at 8), 7.50 (d, J=9 Hz, 1 H, CONH at 5), 7.72 (d, J=7.5 Hz, 1 H, CONH at 7), 8.03 (d, J=10 Hz,1 H, CONH at 2).

[(3 R,4 R)-3-Hydroxy-5-methylthio-N-methyl-L-leucine]$^1$[4'-hydroxy-N-methyl-L-leucine]$^4$-cyclosporin A was prepared according to the following method:

2 cm$^3$ of a 0.5 M sodium methoxide solution were added over 20 minutes to a solution of 0.6 g of [(3 R,4 R)-3-acetyloxy-5-methylthio-N-methyl-L-leucine]$^1$[4'-acetyloxy-N-methyl-L-leucine]$^4$-cyclosporin A in 25 cm$^3$ of methanol. The reaction mixture was stirred at a temperature in the region of 20° C. for 60 hours. The resulting mixture was then concentrated under reduced pressure (2.7 kPa) at a temperature in the region of 30° C. The residue was taken up in 50 cm$^3$ of distilled water. The solid formed was filtered off and washed with a total of 150 cm$^3$ of distilled water. The solid was dried to constant weight and then purified by chromatography on a silica column (0.020–0.045 mm) eluted with a 9/1 (by volume) mixture of ethyl acetate and methanol, and 50-cm$^3$ fractions were collected. The fractions containing the expected product (fractions 9 to 12) were concentrated under reduced pressure (2.7 kPa) at a temperature in the region of 40° C. and gave 0.20 g of [(3 R,4 R)-3-hydroxy-5-methylthio-N-methyl-L-leucine]$^1$[4'-hydroxy-N-methyl-L-leucine]$^4$-cyclosporin A in the form of an amorphous white foam.

$^1$H N.M.R. spectrum (400 MHz, CDCl$_3$, δ in ppm): 1.36 (d, J=7.5 Hz, 3 H, 7β CH$_3$), 1.85 (s, 3 H, 1ε CH$_3$), 2.35 and 2.83 (2 dd, respectively J=13 and 9 Hz and J=13 and 3.5 Hz, each 1 H, 1δ CH$_2$), 2.42 (mt, 1 H, 5β CH), 2.70, 2.72, 3.14, 3.16, 3.26, 3.40 and 3.51 (7 s, each 3 H, the 7 NCH$_3$), 3.18 and 4.69 (2 d, J=14 Hz, each 1 H, 3α CH$_2$), from 3.80 to 3.95 (mt, 2 H, 1β CH and OH at 1β), 4.52 (mt, 1 H, 7α CH), 4.67 (t, J=9 Hz, 1 H, 5α CH), 4.84 (mt, 1 H, 8α CH), from 4.95 to 5.10 (mt, 3 H, 2α CH and α CH of two leucines), 5.15 (d, J=11 Hz, 1 H, 11α CH), 5.42 (d, J=6.5 Hz, 1 H, 1α CH), 5.57 (t, J=5.5 Hz, 1 H, 4α CH), 5.71 (dd, J=11 and 4 Hz, 1 H, α CH of a leucine), 7.21 (d, J=8 Hz, 1 H, CONH at 8), 7.68 (d, J=9 Hz, 1 H, CONH at 5), 7.73 (d, J=7.5 Hz, 1 H, CONH at 7); 8.05 (d, J=10 Hz, 1 H, CONH at 2).

[(3 R,4 R)-3-Acetyloxy-5-methylthio-N-methyl-L-leucine]$^1$[4'-acetyloxy-N-methyl-L-leucine]$^4$-cyclosporin A was prepared according to the following method:

0.56 cm$^3$ of N-methylmorpholine (distilled beforehand) and 0.66 cm$^3$ of isobutyl chloroformate (distilled beforehand) were successively added to a solution, cooled to approximately −15° C. under an inert atmosphere and with light excluded, of 6 g of [(3 R,4 R)-3-acetyloxy-5-carboxy-N-methyl-L-leucine]$^1$[4'-acetyloxy-N-methyl-L-leucine]$^4$-cyclosporin A in 60 cm$^3$ of 1,2-dichloroethane. The reaction mixture was stirred at a temperature in the region of −15° C. for 150 minutes. A solution of 0.700 g of 2-mercaptopyridine N-oxide and of 0.78 cm$^3$ of triethylamine in 15 cm³ of 1,2-dichloroethane was subsequently added over approximately 15 minutes. The reaction mixture was stirred for 17 hours at a temperature in the region of −20° C. before adding, over 10 minutes, 4.09 cm³ of dimethyl disulphide (distilled beforehand). The reaction mixture was irradiated for 3 hours using two 60 W tungsten lamps, the temperature being maintained between 0 and 10° C. The resulting mixture was then concentrated under reduced pressure (2.7 kPA) at a temperature in the region of 40° C. The residue was taken up in 200 cm³ of diethyl ether and 20 cm³ of a 1 N hydrochloric acid solution. The organic phase was separated by seffling and washed successively with a total of 150 cm³ of distilled water, 50 cm³ of a molar aqueous ethanolamine solution and 150 cm³ of distilled water. The organic phase was dried over magnesium sulphate, filtered and then concentrated under reduced pressure (2.7 kPa) at a temperature in the region of 40° C. The residual solid (4 g) was purified by chromatography on a silica column (0.020–0.045 mm) eluted with a 19/1 (by volume) mixture of ethyl acetate and methanol, and 50-cm³ fractions were collected. The fractions containing the expected product (fractions 30 to 35) were concentrated under reduced pressure (2.7 kPa) at a temperature in the region of 40° C. and gave 1.6 g of [(3 R,4 R)-3-acetyloxy-5-methylthio-N-methyl-L-leucine]¹[4'-acetyloxy-N-methyl-L-leucine]⁴-cyclosporin A in the form of an amorphous white foam.

¹H N.M.R. spectrum (400 MHz, CDCl₃, δ in ppm): 1.27 (broad d, J=7.5 Hz, 3 H, 8β CH₃), 1.32 (broad d, J=7.5 Hz, 3 H, 7β CH₃), 1.45 and 1.50 (2 s, each 3 H, the two CH₃ at 4γ), 1.91 (s, 6 H, OCOCH₃ at 4γ and 1ε CH₃), 2.01 (s, 3 H, OCOCH₃ at 1β), 2.30, and 2.54 (respectively dd and broad d, J=16 and 10 Hz and J=16 Hz, each 1 H, 4β CH₂), from 2.35 to 2.50 (mt, 1 H, 5β CH), 2.66, 2.68, 3.10, 3.21, 3.27, 3.30 and 3.46 (7 s, each 3 H, 7 NCH₃), from 3.00 to 3.15 and 4.62 (respectively mt and d, J=14 Hz, each 1 H, 3α CH₂), 4.42 (mt, 1 H, 7α CH), 4.77 (t, J=9 Hz, 1 H, 5α CH), 4.86 (mt, 1 H, 8α CH), from 4.90 to 5.00 (mt, 1 H, 2α CH), 4.99 (d, J=11 Hz, 1 H, 11α CH), 5.12 (mt, 1 H, α CH of a leucine), 5.35 (broad d, J=12 Hz, 1 H, α CH of a leucine), 5.44 (broad d, J=12 Hz, 1 H, 1α CH), 5.53 (broad d, J=12 Hz, 1 H, 1β CH), from 5.60 to 5.75 (mt, 2 H, α CH of a leucine and 4α CH), 7.50 (d, J=8 Hz,1 H, CONH at 8), 7.63 (d, J=9 Hz, 1 H, CONH at 5), 8.08 (d, J=6.5 Hz, 1 H, CONH at 7), 8.51 (d, J=9.5 Hz, 1 H, CONH at 2).

[(3 R,4 R)-3-Acetyloxy-5-carboxy-N-methyl-L-leucine]¹[4'-acetyloxy-N-methyl-L-leucine]⁴-cyclosporin A was prepared according to the following method:

A solution of 7.6 g of sodium carbonate in 200 cm³ of distilled water and then a solution of 15.7 g of sodium metaperiodate in 200 cm³ of distilled water were successively added, while stirring vigorously, to a solution of 12 g of {(4 R)-4-[(E)-buten-2-yl]-O-acetyl-N,4-dimethylthreonine}¹[4'-acetyloxy-N-methyl-L-leucine]⁴-cyclosporin A in 750 cm³ of t-butanol. A solution of 0.29 g of potassium permanganate in 200 cm³ of distilled water was added dropwise over approximately one hour while maintaining the reaction mixture at a temperature of less than 30° C. The reaction mixture was stirred for 36 h at a temperature in the region of 20° C. and then a solution of 0.10 g of potassium permanganate in 70 cm³ of distilled water was added dropwise over approximately 30 minutes. The reaction mixture was stirred at a temperature in the region of 20° C. for 3 hours and then a solution of 47 g of potassium metabisulphite in 200 cm³ of distilled water was added dropwise over approximately 30 minutes. After addition, the reaction mixture was stirred for 15 minutes and then 200 cm³ of a 2 N sulphuric acid solution was added dropwise over approximately 10 minutes. The reaction mixture was extracted with a total of 900 cm³ of diethyl ether. The combined organic phases were dried over magnesium sulphate and then concentrated under reduced pressure (2.7 kPa) at a temperature in the region of 40° C. The residual solid (11.18 g) was stirred for 30 minutes with 300 cm³ of distilled water. The solid obtained was filtered off, washed with a total of 200 cm³ of distilled water and then suspended in 200 cm³ of distilled water. 1.1 cm³ of ethanolamine were added to the suspension obtained. The reaction mixture was stirred for 90 minutes at a temperature in the region of 20° C. The insoluble material was filtered off and the filtrate was extracted with a total of 400 cm³ of diethyl ether. The aqueous phase was acidified to pH=1 with a 5 N hydrochloric acid solution. The reaction mixture was extracted with a total of 700 cm³ of ethyl acetate. The combined organic phases were washed with a total of 200 cm³ of distilled water, dried over magnesium sulphate and then concentrated under reduced pressure (2.7 kPa) at a temperature in the region of 40° C. and gave 6.78 g of [(3 R,4 R)-3-acetyloxy-5-carboxy-N-methyl-L-leucine]¹[4'-acetyloxy-N-methyl-L-leucine]⁴-cyclosporin A in the form of an amorphous white foam.

¹H N.M.R. spectrum (400 MHz, CDCl₃, δ in ppm): 1.91 (s, 3 H, OCOCH₃ at 4γ), 2.02 (s, 3 H, OCOCH₃ at 1β), 2.25 and 2.50 (2 dd, respectively J=16 and 10 Hz and J=16 and 3 Hz, each 1 H, CH₂at 4β), 2.37 (mt,1 H, 5β CH), 2.67, 2.69, 3.11, 3.22, 3.25 and 3.47 (6 s, respectively 3 H, 3 H, 3 H, 6 H, 3 H and 3 H, the 7 NCH₃), 4.45 (mt,1 H, 7α CH), 4.60 (d, J=14 Hz, 1 H, 1 H of the 3α CH₂), 4.80 (mt, 1 H, 5α CH), 4.85 (mt, 1 H, 8α CH), from 4.95 to 5.05 (mt, 1 H, 2α CH), 5.00 (d, J=11 Hz, 1 H, 11α CH), 5.15 (mt, 1 H, α CH of a leucine), from 5.30 to 5.65 (mt, 4 H, α CH of a leucine, 4α CH, 1α CH and 1β CH), 5.68 (dd, J=11 and 4 Hz, 1 H, α CH of a leucine), 7.40 (d, J=8 Hz, 1 H, CONH at 8), 7.71 (d, J=9 Hz, 1 H, CONH at 5), 7.95 (d, J=7.5 Hz, 1 H, CONH at 7), 8.31 (d, J=9.5 Hz, 1 H, CONH at 2).

{(4 R)-4-[(E)-Buten-2-yl]-O-acetyl-N,4-dimethylthreonine}¹[4'-acetyloxy-N-methyl-L-leucine]⁴-cyclosporin A was prepared according to the following method:

10.77 g of 4-dimethylaminopyridine, 12.40 cm³ of triethylamine and 5.6 cm³ of acetic anhydride were successively added to a solution of 17.95 g of [4'-hydroxy-N-methyl-L-leucine]⁴-cyclosporin A in 295 cm³ of dichloromethane. The mixture was stirred for 36 h at a temperature in the region of 20° C. and then 30 cm³ of distilled water were added over approximately 45 minutes. The organic phase was separated by settling, then washed with a total of 180 cm³ of distilled water, dried over magnesium sulphate and then concentrated under reduced pressure (2.7 kPa) at a temperature in the region of 40° C. The residual solid (24.07 g) was stirred for 12 h with 150 cm³ of distilled water. The solid obtained was filtered off, washed with a total of 100 cm³ of distilled water and then dried at atmospheric pressure at a temperature in the region of 20° C. The residual solid (21.45 g) was purified by chromatography on a silica column (0.020–0.045 mm) eluted with a 19/1 (by volume) mixture of ethyl acetate and methanol, and 50-cm³ fractions were collected. The fractions containing the expected product (fractions 7 to 15) were concentrated under reduced pressure (2.7 kPa) at a temperature in the region of 40° C. and gave 10.5 g of {(4 R)4-[(E)-buten-2-yl]-O-acetyl-N,4-dimethylthreonine}¹[4'-acetyloxy-N-methyl-L-leucine]⁴-cyclosporin A in the form of an amorphous white foam which melted at a temperature in the region of 164° C.

¹H N.M.R. spectrum (400 MHz, CDCl₃, δ in ppm): 1.27 (d, J=7 Hz, 3 H, 8β CH₃), 1.33 (d, J=7.5 Hz, 3 H, 7β CH₃), 1.45 and 1.50 (2 s, each 3 H, the two CH₃ at 4γ), 1.59 (d, J=5 Hz, 3 H,1η CH₃), 1.90 (s, 3 H, OCOCH₃ at 4γ), 2.01 (s, 3 H, OCOCH₃ at 1β), 2.31 and 2.55 (2 dd, respectively J=16 and 11 Hz and J=16 and 2 Hz, each 1 H, 4β CH₂), 2.43 (mt, 1 H, 5β CH), 2.65, 2.68, 3.13, 3.20, 3.23, 3.25 and 3.47 (7 s, each 3 H, the 7 NCH₃), 3.08 and 4.62 (2 d, J=14 Hz, each 1 H, 3α CH₂), 4.42 (mt, 1 H, 7α CH), 4.78 (t, J=9 Hz, 1 H, 5α CH), 4.85 (mt, 1 H, 8α CH), 4.45 (mt, 1 H, 2α CH), 4.98 (d, J=11 Hz,1 H, 11α CH), from 5.10 to 5.20 (mt, 2 H, α CH of two leucines), from 5.20 to 5.35 (mt, 2 H, CH=CH), 5.52 (s, 2 H, 1α CH and 1β CH), 5.58 (dd, J=11 and 2 Hz, 1 H, 4α CH), 5.68 (dd, J=11 and 4 Hz, 1 H, α CH of a leucine), 7.42 (d, J=8 Hz, 1 H, CONH at 8), 7.57 (d, J=9 Hz, 1 H, CONH at 5), 8.04 (d, J=7 Hz, 1 H, CONH at 7), 8.51 (d, J=10 Hz, 1 H, CONH at 2).

[4'-Hydroxy-N-methyl-L-leucine]⁴-cyclosporin A was prepared according to the method described in Patent EP 484,281, the disclosure of which is specifically incorporated herein by reference.

EXAMPLE 7

By carrying out the preparations in a way analogous to the methods described in the preceding examples, the following products can be prepared:

[(3 R,4 R)-3-hydroxy-5-methylthio-N-methyl-L-leucine]¹ [(R)-2-aminoethylthio-Sar]³-cyclosporin A;

[(3 R,4 R)-3-hydroxy-5-methylthio-N-methyl-L-leucine]¹[(R)-2-(N-methylamino)ethylthio-Sar]³-cyclosporin A;

[(3 R,4 R)-3-hydroxy-5-methylthio-N-methyl-L-leucine]¹[(R)-2-(N-ethylamino)ethylthio-Sar]³-cyclosporin A;

[(3 R,4 R)-3-hydroxy-5-methylthio-N-methyl-L-leucine]¹[(R)-2-(N-isopropylamino)ethylthio-Sar]³-cyclosporin A;

[(3 R,4 R)-3-hydroxy-5-methylthio-N-methyl-L-leucine]¹[(R)-2-(N-tert-butylamino)ethylthio-Sar]³-cyclosporin A;

[(3 R,4 R)-3-hydroxy-5-methylthio-N-methyl-L-leucine]¹[(R)-2-(N-phenylamino)ethylthio-Sar]³-cyclosporin A;

[(3 R,4 R)-3-hydroxy-5-methylthio-N-methyl-L-leucine]¹[(R)-2-(N-benzylamino)ethylthio-Sar]³-cyclosporin A;

[(3 R,4 R)-3-hydroxy-5-methylthio-N-methyl-L-leucine]¹[(R)-2-(N-methyl-N-ethylamino)ethylthio-Sar]³-cyclosporin A;

[(3 R,4 R)-3-hydroxy-5-methylthio-N-methyl-L-leucine]¹[(R)-2-(N-methyl-N-isopropylamino)ethylthio-Sar]³-cyclosporin A;

[(3 R,4 R)-3-hydroxy-5-methylthio-N-methyl-L-leucine]¹[(R)-2-(N-methyl-N-tert-butylamino)ethylthio-Sar]³-cyclosporin A;

[(3 R,4 R)-3-hydroxy-5-methylthio-N-methyl-L-leucine]¹[(R)-2-(N-methyl-N-allylamino)ethylthio-Sar]³-cyclosporin A;

[(3 R,4 R)-3-hydroxy-5-methylthio-N-methyl-L-leucine]¹[(R)-2-(N-methyl-N-phenylamino)ethylthio- Sar]³-cyclosporin A;

[(3 R,4 R)-3-hydroxy-5-methylthio-N-methyl-L-leucine]¹[(R)-2-(N-methyl-N-benzylamino)ethylthio-Sar]³-cyclosporin A;

[(3 R,4 R)-3-hydroxy-5-methylthio-N-methyl-L-leucine]¹[(R)-2-(N,N-diethylamino)ethylthio-Sar]³-cyclosporin A;

[(3 R,4 R)-3-hydroxy-5-methylthio-N-methyl-L-leucine]¹[(R)-2-(N,N-diisopropylamino)ethylthio-Sar]³-cyclosporin A;

[(3 R,4 R)-3-hydroxy-5-methylthio-N-methyl-L-leucine]¹[(R)-2-(N,N-diallylamino)ethylthio-Sar]³-cyclosporin A;

[(3 R,4 R)-3-hydroxy-5-methylthio-N-methyl-L-leucine]¹[(R)-2-(1-piperidyl)ethylthio-Sar]³-cyclosporin A;

[(3 R,4 R)-3-hydroxy-5-methylthio-N-methyl-L-leucine]¹[(R)-3-aminopropylthio-Sar]³-cyclosporin A;

[(3 R,4 R)-3-hydroxy-5-methylthio-N-methyl-L-leucine]¹[(R)-3-(N-methylamino)propylthio-Sar]³-cyclosporin A;

[(3 R,4 R)-3-hydroxy-5-methylthio-N-methyl-L-leucine]¹[(R)-3-(N-ethylamino)propylthio-Sar]³-cyclosporin A;

[(3 R,4 R)-3-hydroxy-5-methylthio-N-methyl-L-leucine]¹[(R)-3-(N-isopropylamino)propylthio-Sar]³-cyclosporin A;

[(3 R,4 R)-3-hydroxy-5-methylthio-N-methyl-L-leucine]¹[(R)-3-(N-tert-butylamino)propylthio-Sar]³-cyclosporin A;

[(3 R,4 R)-3-hydroxy-5-methylthio-N-methyl-L-leucine]¹[(R)-3-(N-phenylamino)propylthio-Sar]³-cyclosporin A;

[(3 R,4 R)-3-hydroxy-5-methylthio-N-methyl-L-leucine]¹[(R)-3-(N-benzylamino)propylthio-Sar]³-cyclosporin A;

[(3 R,4 R)-3-hydroxy-5-methylthio-N-methyl-L-leucine]¹[(R)-3-(N-methyl-N-ethylamino)propylthio-Sar]³-cyclosporin A;

[(3 R,4 R)-3-hydroxy-5-methylthio-N-methyl-L-leucine]¹[(R)-3-(N-methyl-N-isopropylamino)propylthio-Sar]³-cyclosporin A;

[(3 R,4 R)-3-hydroxy-5-methylthio-N-methyl-L-leucine]¹[(R)-3-(N-methyl-N-tert-butylamino)propylthio-Sar]³-cyclosporin A;

[(3 R,4 R)-3-hydroxy-5-methylthio-N-methyl-L-leucine]¹[(R)-3-(N-methyl-N-allylamino)propylthio-Sar]³-cyclosporin A;

[(3 R,4 R)-3-hydroxy-5-methylthio-N-methyl-L-leucine]¹[(R)-3-(N-methyl-N-phenylamino)propylthio-Sar]³-cyclosporin A;

[(3 R,4 R)-3-hydroxy-5-methylthio-N-methyl-L-leucine]¹[(R)-3-(N-methyl-N-benzylamino)propylthio-Sar]³-cyclosporin A;

[(3 R,4 R)-3-hydroxy-5-methylthio-N-methyl-L-leucine]¹[(R)-2-(N,N-dimethylamino)ethylthio-Sar]³-cyclosporin A;

[(3 R,4 R)-3-hydroxy-5-methylthio-N-methyl-L-leucine]¹[(R)-3-(N,N-diethylamino)propylthio-Sar]³-cyclosporin A;

[(3 R,4 R)-3-hydroxy-5-methylthio-N-methyl-L-leucine]¹[(R)-3-(N,N-diisopropylamino)propylthio-Sar]³-cyclosporin A;

[(3 R,4 R)-3-hydroxy-5-methylthio-N-methyl-L-leucine]¹[(R)-3-(N,N-diallylamino)propylthio-Sar]³-cyclosporin A;

[(3 R,4 R)-3-hydroxy-5-methylthio-N-methyl-L-leucine]¹[(R)-3-(1-piperidyl)propylthio-Sar]³-cyclosporin A;

[(3 R,4 R)-3-hydroxy-5-methylthio-N-methyl-L-leucine]¹[(R)-4-aminobutylthio-Sar]³-cyclosporin A;

[(3 R,4 R)-3-hydroxy-5-methylthio-N-methyl-L-leucine]¹[(R)-4-(N-methylamino)butylthio-Sar]³-cyclosporin A;

[(3 R,4 R)-3-hydroxy-5-methylthio-N-methyl-L-leucine]¹[(R)-4-(N-ethylamino)butylthio-Sar]³-cyclosporin A;

[(3 R,4 R)-3-hydroxy-5-methylthio-N-methyl-L-leucine]¹[(R)-4-(N-isopropylamino)butylthio-Sar]³-cyclosporin A;

[(3 R,4 R)-3-hydroxy-5-methylthio-N-methyl-L-leucine]¹[(R)-4-(N-tert-butylamino)butylthio-Sar]³-cyclosporin A;

[(3 R,4 R)-3-hydroxy-5-methylthio-N-methyl-L-leucine]¹[(R)-4-(N-phenylamino)butylthio-Sar]³-cyclosporin A;

[(3 R,4 R)-3-hydroxy-5-methylthio-N-methyl-L-leucine]¹[(R)-4-(N-benzylamino)butylthio-Sar]³-cycosporin A;

[(3 R,4 R)-3-hydroxy-5-methylthio-N-methyl-L-leucine]¹[(R)-4-(N-methyl-N-ethylamino)butylthio-Sar]³-cyclosporin A;

[(3 R,4 R)-3-hydroxy-5-methylthio-N-methyl-L-leucine]¹[(R)-4-(N-methyl-N-isopropylamino)butylthio-Sar]³-cyclosporin A;

[(3 R,4 R)-3-hydroxy-5-methylthio-N-methyl-L-leucine]¹[(R)-4-(N-methyl-N-tert-butylamino)butylthio-Sar]³-cyclosporin A;

[(3 R,4 R)-3-hydroxy-5-methylthio-N-methyl-L-leucine]¹[(R)-4-(N-methyl-N-allylamino)butylthio-Sar]³-cyclosporin A;

[(3 R,4 R)-3-hydroxy-5-methylthio-N-methyl-L-leucine]¹[(R)-4-(N-methyl-N-phenylamino)butylthio-Sar]³-cyclosporin A;

[(3 R,4 R)-3-hydroxy-5-methylthio-N-methyl-L-leucine]¹[(R)-4-(N-methyl-N-benzylamino)butylthio-Sar]³-cyclosporin A;

[(3 R,4 R)-3-hydroxy-5-methylthio-N-methyl-L-leucine]¹[(R)-4-(N,N-dimethylamino)butylthio-Sar]³-cyclosporin A;

[(3 R,4 R)-3-hydroxy-5-methylthio-N-methyl-L-leucine]¹[(R)-4-(N,N-diethylamino)butylthio-Sar]³-cyclosporin A;

[(3 R,4 R)-3-hydroxy-5-methylthio-N-methyl-L-leucine]¹[(R)-4-(N,N-diisopropylamino)butylthio-Sar]³-cyclosporin A;

[(3 R,4 R)-3-hydroxy-5-methylthio-N-methyl-L-leucine]¹[(R)-4-(N,N-diallylamino)butylthio-Sar]³-cyclosporin A;

[(3 R,4 R)-3-hydroxy-5-methylthio-N-methyl-L-leucine]¹[(R)-4-(1-piperidyl)butylthio-Sar]³- cyclosporin A;

[(3 R,4 R)-3-hydroxy-5-methylthio-N-methyl-L-leucine]¹[(R)-2-amino-2-methylpropylthio-Sar]³-cyclosporin A;

[(3 R,4 R)-3-hydroxy-5-methylthio-N-methyl-L-leucine]¹[(R)-2-(N,N-dimethylamino)-2-methylpropylthio-Sar]³- cyclosporin A;

[(3 R,4 R)-3-hydroxy-5-methylthio-N-methyl-L-leucine]¹[(R)-2-(N,N-diethylamino)-2-methylpropylthio-Sar]³-cyclosporin A;

[(3 R,4 R)-3-hydroxy-5-methylthio-N-methyl-L-leucine]¹[(R)-2-(1-piperidyl)-2-methylpropylthio-Sar]³-cyclosporin A;

[(3 R,4 R)-3-hydroxy-5-methylthio-N-methyl-L-leucine]¹[(R)-3-amino-3-methylbutylthio-Sar]³-cyclosporin A;

[(3 R,4 R)-3-hydroxy-5-methylthio-N-methyl-L-leucine]¹[(R)-3-(N,N-dimethylamino)-3-methylbutylthio-Sar]³-cyclosporin A;

[(3 R,4 R)-3-hydroxy-5-methylthio-N-methyl-L-leucine]¹[(R)-3-(N,N-diethylamino)-3-methylbutylthio-Sar]³-cyclosporin A;

[(3 R,4 R)-3-hydroxy-5-methylthio-N-methyl-L-leucine]¹[(R)-3-(1-piperidyl)-3-methylbutylthio-Sar]³-cyclosporin A;

[(3 R,4 R)-3-hydroxy-5-methylthio-N-methyl-L-leucine]¹[(R)-2-(1-morpholino)ethylthio-Sar]³-cyclosporin A;

[(3 R,4 R)-3-hydroxy-5-methylthio-N-methyl-L-leucine]¹[(R)-2-(1-azetidino)ethylthio-Sar]³-cyclosporin A;

[(3 R,4 R)-3-hydroxy-5-methylthio-N-methyl-L-leucine]¹{(R)-2-[1-(4-methylpiperazino)]ethylthio-Sar}³-cyclosporin A;

[(3 R,4 R)-3-hydroxy-5-methylthio-N-methyl-L-leucine]¹{(R)-2-[1-(4-phenylpiperazino)]ethylthio-Sar}³-cyclosporin A;

[(3 R,4 R)-3-hydroxy-5-methylthio-N-methyl-L-leucine]¹{(R)-2-[1-(4-benzylpiperazino)]ethylthio-Sar}³-cyclosporin A;

[(3 R,4 R)-3-hydroxy-5-methylthio-N-methyl-L-leucine]¹{(R)-2-[1-(4-methyl-1,2,3,6-tetrahydropyridyl)]ethylthio-Sar}³-cyclosporin A;

[(3 R,4 R)-3-hydroxy-5-methylthio-N-methyl-L-leucine]¹{(R)-2-[1-(4-phenyl-1,2,3,6-tetrahydropyridyl)]ethylthio-Sar}³-cyclosporin A;

[(3 R,4 R)-3-hydroxy-5-methylthio-N-methyl-L-leucine]¹[(R)-3-(1-morpholino)propylthio-Sar]³-cyclosporin A;

[(3 R,4 R)-3-hydroxy-5-methylthio-N-methyl-L-leucine]¹[(R)-3-(1-azetidino)propylthio-Sar]³-cyclosporin A;

[(3 R,4 R)-3-hydroxy-5-methylthio-N-methyl-L-leucine]¹{(R)-3-[1-(4-methylpiperazino)]propylthio-Sar}³-cyclosporin A;

[(3 R,4 R)-3-hydroxy-5-methylthio-N-methyl-L-leucine]¹{(R)-3-[1-(4-phenylpiperazino)]propylthio-Sar}³-cyclosporin A;

[(3 R,4 R)-3-hydroxy-5-methylthio-N-methyl-L-leucine]¹{(R)-3-[1-(4-benzylpiperazino)]propylthio-Sar}³-cyclosporin A;

[(3 R,4 R)-3-hydroxy-5-methylthio-N-methyl-L-leucine]¹{(R)-3-[1-(4-methyl-1,2,3,6-tetrahydropyridyl)]propylthio-Sar}³-cyclosporin A;

[(3 R,4 R)-3-hydroxy-5-methylthio-N-methyl-L-leucine]¹{(R)-3-[1-(4-methyl-1,2,3,6-tetrahydropyridyl)]propylthio-Sar}³-cyclosporin A;

[(3 R,4 R)-3-hydroxy-5-methylthio-N-methyl-L-leucine]¹[(R)-2-methylthio-Sar]³-[4'-hydroxy-MeLeu]⁴-cyclosporin A;

[(3 R,4 R)-3-hydroxy-5-methylthio-N-methyl-L-leucine]¹[(R)-2-aminoethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-ethylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-isopropylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-tert-butylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-phenylamino)ethylthio-Sar]3-[4'-hydroxy-MeLeu]⁴-cyclosporin A;

[(3 R,4 R)-3-hydroxy-5-methylthio-N-methyl-L-leucine]¹[(R)-2-(N-benzylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-ethylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-isopropylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-tert-butylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-allylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-phenylamino)ethylthio- Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-benzylamino)ethylthio- Sar]³-[4'-hydroxy-MeLeu]⁴-cyclosporin A;

[(3 R,4 R)-3-hydroxy-5-methylthio-N-methyl-L-leucine]¹[(R)-2-(N,N-diethylamino)ethylthio-Sar]³-[4'-hydroxy-MeLeu]⁴-cyosporin A;

[(3 R,4 R)-3-hydroxy-5-methylthio-N-methyl-L-leucine]¹[(R)-2-(N,N-diisopropylamino)ethylthio] Sar ³-[4'-hydroxy-MeLeu]⁴-cyclosporin A;

[(3 R,4 R)-3-hydroxy-5-methylthio-N-methyl-L-leucine]¹[(R)-2-(N,N-diallylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(1-piperidyl)ethylthio-Sar]³-[4'-hydroxy-eLeu]⁴-cyclosporin A;

[(3 R,4 R)-3-hydroxy-5-methylthio-N-methyl-L-leucine]¹[(R)-3-aminopropylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-ethylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-isopropylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-tert-butylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-phenylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-benzylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-ethylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-isopropylamino)propylthio-Sar]³-[4'-hydroxy-MeLeu⁴-cycosporin A;

[(3 R,4 R)-3-hydroxy-5-methylthio-N-methyl-L-leucine]¹[(R)-3-(N-methyl-N-tert-butylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-allylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-phenylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-benzylamino)propylthio-Sar]³-[4'-hydroxy-MeLeu]⁴-cyclosporin A;

[(3 R,4 R)-3-hydroxy-5-methylthio-N-methyl-L-leucine]¹[(R)-2-(N,N-dimethylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-3-(N,N-diethyiamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N,N-diisopropylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N,N-diallylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(1-piperidyl)propylthio-Sar]³-[4'-hydroxy-MeLeu]⁴-cycosporin A;

[(3 R,4 R)-3-hydroxy-5-methylthio-N-methyl-L-leucine]¹[(R)-4-aminobutylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-ethylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-isopropylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-tert-butylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-phenylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-benzylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-ethylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-isopropylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-tert-butylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-allylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-phenylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-benzylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N,N-dimethylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N,N-diethylamino)butylthio-Sar]³[4'-hydroxy-MeLeu]⁴-cyclosporin A;

[(3 R,4 R)-3-hydroxy-5-methylthio-N-methyl-L-leucine]¹[(R)-4-(N,N-diisopropylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N,N-diallylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(1-piperidyl)butylthio-Sar]³-[4'-hydroxy-MeLeu]⁴-cyclosporin A;

[(3 R,4 R)-3-hydroxy-5-methylthio-N-methyl-L-leucine]¹[(R)-2-amino-2-methylpropylthio-Sar]³-[4'-hydroxy-MeLeu]⁴-cyclosporin A;

[(3 R,4 R)-3-hydroxy-5-methylthio-N-methyl-L-leucine]¹[(R)-2-(N,N-dimethylamino)-2-methylpropylthio-Sar]³-[4'-hydroxy-MeLeu]⁴-cyclosporin A;

[(3 R,4 R)-3-hydroxy-5-methylthio-N-methyl-L-leucine]¹[(R)-2-(N,N-diethylamino)-2-methylpropylthio-Sar]³-[4'-hydroxy-MeLeu]⁴-cyclosporin A;

[(3 R,4 R)-3-hydroxy-5-methylthio-N-methyl-L-leucine]¹[(R)-2-(1-piperidyl)-2-methylpropylthio-Sar]³- [4'-hydroxy-MeLeu]⁴-cyclosporin A;

[(3 R,4 R)-3-hydroxy-5-methylthio-N-methyl-L-leucine]¹[(R)-3-amino-3-methylbutylthio-Sar]³-[4'-hydroxy-MeLeu]⁴-cyclosporin A;

[(3 R,4 R)-3-hydroxy-5-methylthio-N-methyl-L-leucine]¹[(R)-3-(N,N-dimethylamino))-3-methylbutylthio-Sar]³-[4'-hydroxy-MeLeu]⁴-cyclosporin A;

[(3 R,4 R)-3-hydroxy-5-methylthio-N-methyl-L-leucine]¹ [(R)-3-(N,N-diethylamino)-3-methylbutylthio-Sar]³-[4'-hydroxy-MeLeu]⁴-cyclosporin A;

[(3 R,4 R)-3-hydroxy-5-methylthio-N-methyl-L-leucine]¹[(R)-3-(1-piperidyl)-3-methylbutylthio-Sar]³-[4'-hydroxy-MeLeu]⁴-cyclosporin A;

[(3 R,4 R)-3-hydroxy-5-methylthio-N-methyl-L-leucine]¹[(R)-2-(1-morpholino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(1-azetid ino)ethylthio-Sar]³-[4'-hydroxy-MeLeu]⁴-cyclosporin A;

[(3 R,4 R)-3-hydroxy-5-methylthio-N-methyl-L-leucine]¹{(R)-2-[1-(4-methylpiperazino)]ethylthio-Sar}³-[4'-hydroxy-MeLeu]⁴-cyclosporin A;

[(3 R,4 R)-3-hydroxy-5-methylthio-N-methyl-L-leucine]¹{(R)-2-[1-(4phenylpiperazino)]ethylthio-Sar}³-4'-hroxy-MeLeU]⁴-Cyclosporin A;

[(3 R,4 R)-3-hydroxy-5-methylthio-N-methyl-L-leucine]¹{(R)-2-[1-(4-benzylpiperazino)]ethylthio-Sar}³-[4'-hydroxy-MeLeu]⁴-cyclosporin A;

[(3 R,4 R)-3-hydroxy-5-methylthio-N-methyl-L-leucine]¹{(R)-2-[1-(4-methyl-1,2,3,6-tetrahydropyridyl)]ethylthio-Sar}³-[4'-hydroxy-MeLeu]⁴-cyclosporin A;

[(3 R,4 R)-3-hydroxy-5-methylthio-N-methyl-L-leucine]¹{(R)-2-[1-(4-phenyl-1,2,3,6-tetrahydropyridyl)]ethylthio-Sar}³-[4'-hydroxy-MeLeu]⁴-cyclosporin A;

[(3 R,4 R)-3-hydroxy-5-methylthio-N-methyl-L-leucine]¹[(R)-3-(1-morpholino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(1-azetidino)propylthio-Sar]³-[4'-hydroxy-MeLeu]⁴-cyclosporin A;

[(3 R,4 R)-3-hydroxy-5-methylthio-N-methyl-L-leucine]¹{(R)-3-[1-(4-methylpiperazino)]propylthio-Sar}³-[4'-hydroxy-MeLeu]⁴-cyclosporin A;

[(3 R,4 R)-3-hydroxy-5-methylthio-N-methyl-L-leucine]¹{(R)-3-[1-(4-phenylpiperazino)]propylthio-Sar}³-[4'-hydroxy-MeLeu]⁴-cyclosporin A;

[(3 R,4 R)-3-hydroxy-5-methylthio-N-methyl-L-leucine]¹{(R)-3-[1-(4-benzylpiperazino)]propylthio-Sar}³-[4'-hydroxy-MeLeu]⁴-cyclosporin A;

[(3 R,4 R)-3-hydroxy-5-methylthio-N-methyl-L-leucine]¹{(R)-3-[1-(4-methyl-1,2,3,6-tetrahydropyridyl)]propylthio-Sar}³-[4'-hydroxy-MeLeu]⁴-cyclosporin A;

[(3 R,4 R)-3-hydroxy-5-methylthio-N-methyl-L-leucine]¹{(R)-3-[1-(4-methyl-1,2,3,6-tetrahydropyridyl)]propylthio-Sar}³-[4'-hydroxy-MeLeu]⁴-cyclosporin A.

The present invention also relates to pharmaceutical compositions containing at least one product of formula (I), if appropriate in the salt form, in the pure state, i.e., alone, or in the form of a combination with one or more compatible and pharmaceutically acceptable diluents or adjuvants or with another anti-retrovirus agent, optionally intended for the treatment of AIDS, or an antiviral, immunomodulating or antimicrobial agent.

The composition according to the invention is preferably capable of keeping alive cells infected with a retrovirus, such as, for example, the HIV, and thus of reducing progression towards AIDS or of decreasing its seriousness in subjects already infected by reducing the mortality of infected cells. The compositions of the invention can be used orally, parenterally, rectally or in aerosols.

The pharmaceutical compositions according to the invention can preferably be used curatively or preventively in subjects exhibiting immunodeficiency and/or infected by a retrovirus. Of course, the make-up of these compositions will be suited to the specific case of the digestive system of the immunodepressed subjects.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate.

These compositions can also contain adjuvants, in particular wetting, isotonizing, emulsifying, dispersing and stabilizing agents.

Sterilization can be carried out in several ways, for example using a bacteriological filter, by irradiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle with a particle size of 30 to 80 μm, for example dextran, mannitol or lactose.

In human therapeutics, the doctor will determine the posology which (s)he considers the most appropriate according to a preventive or curative treatment and according to the age, weight, stage of the infection and other factors specific to the subject to be treated. Generally, doses range from 5 to 30 mg/kg by the oral route for an adult.

In addition, it has been shown that cyclosporin derivatives of formula (I) can preferably display a synergic effect when they are combined with other antiviral agents which are active with respect to retroviruses. The present invention also relates to synergizing combinations which contain at least one cyclosporin derivative of formula (I) and/or, if appropriate, their salts and an active principle known for its activity with respect to retroviruses.

The agents known for their activity with respect to retroviruses which can be combined are chosen from agents which are compatible and inert with respect to the cyclosporin derivative of formula (I), both in the category of pharmacological treatments and in the category of alternative treatments, such as gene and cell or antisense therapy. Without implied limitation, these agents constituting the various therapeutic classes are chosen, for example, from nucleoside reverse transcriptase inhibitors (NRTI) and non-nucleoside reverse transcriptase inhibitors (NNRTI) [zidovudine (AZT), didanosine (DDI), dideoxycytidine (DDC), d4T, ribavirin, 3TC, nevirapin, and the like], from protease inhibitors [such as, for example, Saquinavir, Ritonavir, Indinavir and Nelfinavir], integrase inhibitors [such as AR177], from therapy gene inhibitors targeting the regulatory proteins of HIV replication, such as inhibitors of the rev protein [such as, for example, Rev M10], or nucleocapsid inhibitors [such as, for example, DIBAs], from inhibitors targeting the specific messenger RNA transcripts of all the HIVs, such as, for example, the antisense ones [such as GEM92, GPI-2A and the like], from inhibitors of the family of modulators of cellular dNTP [such as hydroxyurea], from cytokine inhibitors [such as TNF], from inhibitors of entry of HIVs [such as T20, SPC-3, and the like], and from agents constituting therapeutic classes used in vaccinal approaches, both by biotechnology [such as HIVAC-1e, ALVAC, and the like] and by compounds acting with respect to the immune response [such as RG-8394].

The pharmaceutical compositions comprising such combinations, optionally in the presence of pharmaceutically acceptable excipients, also come within the scope of the present invention.

The following example illustrates a composition according to the invention.

FORMULATION EXAMPLE

A formulation was prepared which can be administered by the oral route and which had the following composition:

| | |
|---|---|
| [(3R,4R)-3-hydroxy-5-methylthio-N-methyl-L-leucine]$^1$[(2R)-2'-(diethylamino)ethyl-thiosarcosine]$^3$-cyclosporin A | 250 mg |
| Magnesium stearate | 3 mg |
| Acdisol | 15 mg |
| Colloidal silica | 2 mg |
| Lactose | 130 mg |

What is claimed is:
1. A cyclosporin compound of formula (I):

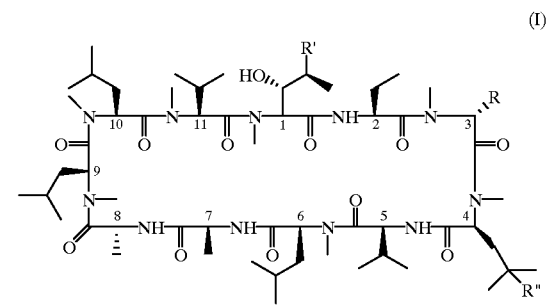

in which:

R is a hydrogen atom or a radical of formula (Ia):

in which

Alk-R° represents a methyl radical, or alternatively

Alk represents a $C_{2-6}$ straight chain or branched alkylene radical or a $C_{3-6}$ cycloalkylene radical, and R° represents a hydrogen atom or a hydroxyl, carboxyl or alkyloxy-carbonyl radical, or an —NR$_1$R$_2$ radical in which R$_1$ and R$_2$, which are identical or different, represent a hydrogen atom or a phenyl, alkyl, $C_{2-4}$ alkenyl or $C_{3-6}$ cycloalkyl radical, said radical optionally substituted with selected from a halogen atom, an alkyloxy, alkyloxycarbonyl, amino, alkylamino and dialkylamino radical; or R$_1$ and R$_2$ represent a benzyl or saturated or unsaturated heterocyclyl radical, said radical containing from 5 to 6 ring members and from 1 to 3 heteroatoms;

or in which R$_1$ and R$_2$ form, together with the nitrogen atom to which they are attached, a saturated or unsaturated 4- to 6-membered heterocycle, which heterocycle having an additional heteroatom selected from nitrogen, oxygen and sulphur, and wherein said saturated or unsaturated heterocycle is optionally substituted by an alkyl, phenyl or benzyl radical, or a radical of the formula (Ib):

$$-N(R_3)-(CH_2)_n-N(R_1)(R_2) \quad (Ib)$$

in which $R_1$ and $R_2$ are as defined above, $R_3$ represents a hydrogen atom or an alkyl radical and n is an integer ranging from 2 to 4, R' represents a radical of formula (Ic) or (Id):

$$-CH_2-CH=CH-CH_2-R_4 \text{ (Ic) or } -CH_2-S-R'_4 \quad (Id)$$

in which $R_4$ represents an alkylthio, aminoalkylthio, alkylaminoalkylthio, dialkylaminoalkylthio, pyrimidinylthio, thiazolylthio, N-alkylimidazolylthio, hydroxyalkylphenylthio, hydroxyalkylphenyloxy, nitrophenylamino or 2-oxopyrimidin-1-yl radical and $R'_4$ represents an alkyl radical, and R" represents a hydrogen atom or a hydroxyl radical, with the proviso that R and R" are not simultaneously a hydrogen atom, and wherein the alkyl portions or radicals defined above are straight chain or branched and contain from 1 to 4 carbon atoms, or a pharmaceutically acceptable salt thereof.

2. A cyclosporin compound of formula (I) according to claim 1, wherein R is a hydrogen atom or a radical of formula (Ia) as defined in claim 1, in which Alk-R° represents a methyl radical, or Alk represents a $C_{2-6}$ straight chain or branched alkylene radical, and R° represents an $-NR_1R_2$ radical in which $R_1$ and $R_2$, which are identical or different, each represent an alkyl radical, R' represents a radical of formula (Ic) or (Id):

$$-CH_2-CH=CH-CH_2-R_4 \text{ (Ic) or } -CH_2-S-R'_4 \quad (Id)$$

in which $R_4$ represents an alkylthio radical and $R'_4$ represents an alkyl radical, and R" represents a hydrogen atom or a hydroxyl radical, with the proviso that R and R" are not simultaneously a hydrogen atom, and wherein the alkyl portions or radicals defined above are straight chain or branched and contain from 1 to 4 carbon atoms, or a pharmaceutically acceptable salt thereof.

3. A cyclosporin compound of formula (I) according to claim 1, wherein R is a radical of formula (Ia) as defined in claim 1, in which Alk-R' represents a methyl radical, or Alk represents an ethylene radical and R° represents an $-NR_1R_2$ radical in which $R_1$ and $R_2$, which are identical or different, each represent a $C_{1-2}$ alkyl radical, R' represents a radical of formula (Ic) or (Id):

$$-CH_2-CH=CH-CH_2-R_4 \text{ (Ic) or } -CH_2-S-R'_4 \quad (Id)$$

in which $R_4$ represents a methylthio radical and $R'_4$ represents a methyl radical, and R" represents a hydrogen atom or a hydroxyl radical, or R is a hydrogen atom, R' is as defined above and R" is a hydroxyl radical, or a pharmaceutically acceptable salt thereof.

4. [(3 R,4 R)-3-hydroxy-5-methylthio-N-methyl-L-leucine]¹[(2 R)-methylthio-sarcosine]³-cyclosporin A, or a pharmaceutically acceptable salt thereof.

5. [(3 R,4 R)-3-hydroxy-5-methylthio-N-methyl-L-leucine]¹[(2 R)-2'-(diethylamino)ethylthiosarcosine]³-cyclosporin A, or a pharmaceutically acceptable salt thereof.

6. [(3 R,4 R)-3-hydroxy-5-methylthio-N-methyl-L-leucine]¹[4-hydroxy-N-methyl- leucine]⁴-cyclosporin A, or a pharmaceutically acceptable salt thereof.

7. [(4 R)-4-((E)-4-(methylthio)buten-2-yl)-N,4-dimethylthreonine]¹-[(2 R)-2'-(diethylamino)ethylthio-sarcosine]³-cyclosporin A, or a pharmaceutically acceptable salt thereof.

8. [(3 R,4 R)-3-hydroxy-5-methylthio-N-methyl-L-leucine]¹[(2 R)-2'-(dimethyl-amino)ethylthio-sarcosine]³ [4'-hydroxy-N-methyl-L- leucine]⁴-cyclosporin A, or a pharmaceutically acceptable salt thereof.

9. A process for preparing a cyclosporin compound of formula (I) according to claim 1, or a pharmaceutically acceptable salt thereof, in which R' is a radical of formula (Ic) as defined in claim 1, which process comprises:

reacting, in a basic medium, an 8'-bromo-3-acetoxycyclosporin of the formula (II):

(II)

in which R" is as defined above, with a thiol of the formula (IIIa):

HS—R"₄ (IIIa)

in which R"₄ represents an alkyl, aminoalkyl, alkylaminoalkyl, dialkylaminoalkyl, pyridinyl, thiazolyl, N-alkylimidazolyl or hydroxyalkylphenyl radical, or with a phenol of the formula (IIIb):

HO—R'"₄ (IIIb)

in which R'"₄ represents a hydroxyalkylphenyl radical, or with an amine of the formula (IIIc):

H₂N—R""₄ (IIIc)

in which R""₄ represents a nitrophenyl radical or a radical of 2-oxopyrimidine, subsequently removing the 3'-acetoxy protective radical of the hydroxyl radical on the chain at the 1-position, when R" in the starting cyclosporin compound of formula (II) is hydrogen, optionally hydroxylating at the 4'-position of the [MeLeu]⁴ residue, to obtain a derivative in which R" is hydroxyl, and/or substituting the chain of formula (Ia) as defined in claim 1 to obtain a cyclosporin derivative in which R is other than a hydrogen atom, and optionally converting said cyclosporin into a salt.

10. A process for preparing a cyclosporin compound of formula (I) according to claim 1, or a pharmaceutically acceptable salt thereof, in which R' is a radical of formula (Id) as defined in claim 1, which process comprises:

converting a mixed anhydride of an acid of formula (V):

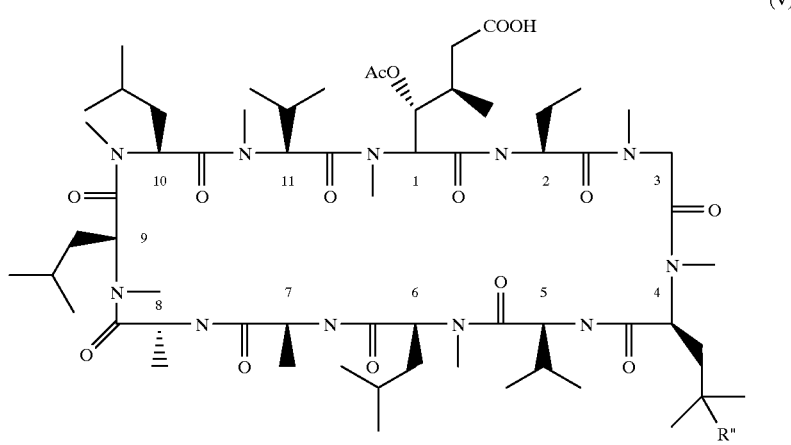

(V)

in which R" is as defined above and Ac represents an acetyl radical, to a thiohydroxamic ester by reacting said acid of formula (V with a salt of N-hydroxy-2-thiopyridine, with the exclusion of light, photochemically converting said thiohydroxamic ester obtained by irradiation, in the presence of a disulphide of formula (IV):

R'₄—S—S—R'₄ (IV)

in which R'₄ is as defined in claim 1, freeing said photochemically converted product from the hydroxy-protective acetyl radical, to obtain a compound in which R' is a radical of formula (Id) as defined in claim 1, when R" in the starting cyclosporin compound of formula (II) is hydrogen, optionally hydroxylating at the 4'-position of the [MeLeu]⁴ residue to obtain a derivative in which R" is hydroxyl, and/or substituting the chain of formula (Ia) as defined in claim 1 to obtain a cyclosporin derivative in which R is other than a hydrogen atom, and optionally converting said cyclosporin into a salt.

11. A pharmaceutical composition, said composition comprising at least one cyclosporin compound according to claim 1, and at least one compatible and pharmaceutically acceptable diluent or adjuvant.

12. A pharmaceutical composition, said composition comprising at least one cyclosporin compound according to claim 1 and at least one antiviral, immunomodulating or antimicrobial active principle.

13. A compound selected from the group consisting of:

[(3 R,4 R)-3-hydroxy-5-methylthio-N-methyl-L-leucine]¹[(R)-2-aminoethylthio-Sar]³-cyclosporin A;

[(3 R,4 R)-3-hydroxy-5-methylthio-N-methyl-L-leucine]¹[(R)-2-(N-methylamino)ethylthio-Sar]³-cyclosporin A;

[(3 R,4 R)-3-hydroxy-5-methylthio-N-methyl-L-leucine]¹[(R)-2-(N-ethylamino)ethylthio-Sar]³-cyclosporin A;

[(3 R,4 R)-3-hydroxy-5-methylthio-N-methyl-L-leucine]¹[(R)-2-(N-isopropylamino)ethylthio-Sar]³-cyclosporin A;

[(3 R,4 R)-3-hydroxy-5-methylthio-N-methyl-L-leucine]¹[(R)-2-(N-tert-butylamino)ethylthio-Sar]³-cyclosporin A;

[(3 R,4 R)-3-hydroxy-5-methylthio-N-methyl-L-leucine]¹[(R)-2-(N-phenylamino)ethylthio-Sar]³-cyclosporin A;

[(3 R,4 R)-3-hydroxy-5-methylthio-N-methyl-L-leucine]¹[(R)-2-(N-benzylamino)ethylthio-Sar]³-cyclosporin A;

[(3 R,4 R)-3-hydroxy-5-methylthio-N-methyl-L-leucine]¹[(R)-2-(N-methyl-N-ethylamino)ethylthio-Sar]³-cyclosporin A;

[(3 R,4 R)-3-hydroxy-5-methylthio-N-methyl-L-leucine]¹[(R)-2-(N-methyl-N-isopropylamino)ethylthio-Sar]³-cyclosporin A;

[(3 R,4 R)-3-hydroxy-5-methylthio-N-methyl-L-leucine]¹[(R)-2-(N-methyl-N-tert-butylamino)ethylthio-Sar]³-cyclosporin A;

[(3 R,4 R)-3-hydroxy-5-methylthio-N-methyl-L-leucine]¹[(R)-2-(N-methyl-N-allylamino)ethylthio-Sar]³-cyclosporin A;

[(3 R,4 R)-3-hydroxy-5-methylthio-N-methyl-L-leucine]¹[(R)-2-(N-methyl-N-phenylamino)ethylthio-Sar]³-cyclosporin A;

[(3 R,4 R)-3-hydroxy-5-methylthio-N-methyl-L-leucine]¹[(R)-2-(N-methyl-N-benzylamino)ethylthio-Sar]³-cyclosporin A;

[(3 R,4 R)-3-hydroxy-5-methylthio-N-methyl-L-leucine]¹[(R)-2-(N,N-diethylamino)ethylthio-Sar]³-cyclosporin A;

[(3 R,4 R)-3-hydroxy-5-methylthio-N-methyl-L-leucine]¹[(R)-2-(N,N-diisopropylamino)ethylthio-Sar]³-cycosporin A;

[(3 R,4 R)-3-hydroxy-5-methylthio-N-methyl-L-leucine]¹[(R)-2-(N,N-diallylamino)ethylthio-Sar]³-cyclosporin A;

[(3 R,4 R)-3-hydroxy-5-methylthio-N-methyl-L-leucine]¹[(R)-2-(1-piperidyl)ethylthio-Sar]³-cyclosporin A;

[(3 R,4 R)-3-hydroxy-5-methylthio-N-methyl-L-leucine]¹[(R)-3-aminopropylthio-Sar]³-cyclosporin A;

[(3 R,4 R)-3-hydroxy-5-methylthio-N-methyl-L-leucine]¹[(R)-3-(N-methylamino)propylthio-Sar]³-cyclosporin A;

[(3 R,4 R)-3-hydroxy-5-methylthio-N-methyl-L-leucine]¹[(R)-3-(N-ethylamino)propylthio-Sar]³-cyclosporin A;

[(3 R,4 R)-3-hydroxy-5-methylthio-N-methyl-L-leucine]¹[(R)-3-(N-isopropylamino)propylthio-Sar]³-cyclosporin A;

[(3 R,4 R)-3-hydroxy-5-methylthio-N-methyl-L-leucine]¹[(R)-3-(N-tert-butylamino)propylthio-Sar]³-cyclosporin A;

[(3 R,4 R)-3-hydroxy-5-methylthio-N-methyl-L-leucine]¹[(R)-3-(N-phenylamino)propylthio-Sar]³-cyclosporin A;

[(3 R,4 R)-3-hydroxy-5-methylthio-N-methyl-L-leucine]¹[(R)-3-(N-benzylamino)propylthio-Sar]³-cyclosporin A;

[(3 R,4 R)-3-hydroxy-5-methylthio-N-methyl-L-leucine]¹[(R)-3-(N-methyl-N-ethylamino)propylthio-Sar]³-cyclosporin A;

[(3 R,4 R)-3-hydroxy-5-methylthio-N-methyl-L-leucine]¹[(R)-3-(N-methyl-N-isopropylamino)propylthio-Sar]³-cyclosporin A;

[(3 R,4 R)-3-hydroxy-5-methylthio-N-methyl-L-leucine]¹[(R)-3-(N-methyl-N-tert-butylamino)propylthio-Sar]³-cyclosporin A;

[(3 R,4 R)-3-hydroxy-5-methylthio-N-methyl-L-leucine]¹[(R)-3-(N-methyl-N-allylamino)propylthio-Sar]³-cyclosporin A;

[(3 R,4 R)-3-hydroxy-5-methylthio-N-methyl-L-leucine]¹[(R)-3-(N-methyl-N-phenylamino)propylthio-Sar]³-cyclosporin A;

[(3 R,4 R)-3-hydroxy-5-methylthio-N-methyl-L-leucine]¹[(R)-3-(N-methyl-N-benzylamino) ropylthio-Sar]³-cyclosporin A;

[(3 R,4 R)-3-hydroxy-5-methylthio-N-methyl-L-leucine]¹[(R)-2-(N,N-dimethylamino)ethylthio-Sar]³-cyclosporin A;

[(3 R,4 R)-3-hydroxy-5-methylthio-N-methyl-L-leucine]¹[(R)-3-(N,N-diethylamino)propylthio-Sar]³-cyclosporin A;

[(3 R,4 R)-3-hydroxy-5-methylthio-N-methyl-L-leucine]¹[(R)-3-(N,N-diisopropylamino)propylthio-Sar]³-cyclosporin A;

[(3 R,4 R)-3-hydroxy-5-methylthio-N-methyl-L-leucine]¹[(R)-3-(N,N-diallylamino)propylthio-Sar]³-cyclosporin A;

[(3 R,4 R)-3-hydroxy-5-methylthio-N-methyl-L-leucine]¹[(R)-3-(1-piperidyl)propylthio-Sar]³-cyclosporin A;

[(3 R,4 R)-3-hydroxy-5-methylthio-N-methyl-L-leucine]¹[(R)-4-aminobutylthio-Sar]³-cyclosporin A;

[(3 R,4 R)-3-hydroxy-5-methylthio-N-methyl-L-leucine]¹[(R)-4-(N-methylamino)butylthio-Sar]³-cyclosporin A;

[(3 R,4 R)-3-hydroxy-5-methylthio-N-methyl-L-leucine]¹[(R)-4-(N-ethylamino)butylthio-Sar]³-cyclosporin A;

[(3 R,4 R)-3-hydroxy-5-methylthio-N-methyl-L-leucine]¹[(R)-4-(N-isopropylamino)butylthio-Sar]³-cyclosporin A;

[(3 R,4 R)-3-hydroxy-5-methylthio-N-methyl-L-leucine]¹[(R)-4-(N-tert-butylamino)butylthio-Sar]³-cyclosporin A;

[(3 R,4 R)-3-hydroxy-5-methylthio-N-methyl-L-leucine]¹[(R)-4-(N-phenylamino)butylthio-Sar]³-cyclosporin A;

[(3 R,4 R)-3-hydroxy-5-methylthio-N-methyl-L-leucine]¹[(R)-4-(N-benzylamino)butylthio-Sar]³-cyclosporin A;

[(3 R,4 R)-3-hydroxy-5-methylthio-N-methyl-L-leucine]¹[(R)-4-(N-methyl-N-ethylamino)butylthio-Sar]³-cyclosporin A;

[(3 R,4 R)-3-hydroxy-5-methylthio-N-methyl-L-leucine]¹[(R)-4-(N-methyl-N-isopropylamino)butylthio-Sar]³-cyclosporin A;

[(3 R,4 R)-3-hydroxy-5-methylthio-N-methyl-L-leucine]¹[(R)-4-(N-methyl-N-tert-butylamino)butylthio-Sar]³-cyclosporin A;

[(3 R,4 R)-3-hydroxy-5-methylthio-N-methyl-L-leucine]¹[(R)-4-(N-methyl-N-allylamino)butylthio-Sar]³-cyclosporin A;

[(3 R,4 R)-3-hydroxy-5-methylthio-N-methyl-L-leucine]¹[(R)-4-(N-methyl-N-phenylamino)butylthio-Sar]3-cyclosporin A;

[(3 R,4 R)-3-hydroxy-5-methylthio-N-methyl-L-leucine]¹[(R)-4-(N-methyl-N-benzylamino)butylthio-Sar]³-cyclosporin A;

[(3 R,4 R)-3-hydroxy-5-methylthio-N-methyl-L-leucine]¹[(R)-4-(N,N-dimethylamino)butylthio-Sar]³-cyclosporin A;

[(3 R,4 R)-3-hydroxy-5-methylthio-N-methyl-L-leucine]¹[(R)-4-(N,N-diethylamino)butylthio-Sar]³-cyclosporin A;

[(3 R,4 R)-3-hydroxy-5-methylthio-N-methyl-L-leucine]¹[(R)-4-(N,N-diisopropylamino)butylthio-Sar]³-cyclosporin A;

[(3 R,4 R)-3-hydroxy-5-methylthio-N-methyl-L-leucine]¹[(R)-4-(N,N-diallylamino)butylthio-Sar]³-cyclosporin A;

[(3 R,4 R)-3-hydroxy-5-methylthio-N-methyl-L-leucine]¹[(R)-4-(1-piperidyl)butylthio-Sar]³-cyclosporin A;

[(3 R,4 R)-3-hydroxy-5-methylthio-N-methyl-L-leucine]¹[(R)-2-amino-2-methylpropylthio-Sar]³-cyclosporin A;

[(3 R,4 R)-3-hydroxy-5-methylthio-N-methyl-L-leucine]¹[(R)-2-(N,N-dimethylamino)-2-methylpropylthio-Sar]³-cyclosporin A;

[(3 R,4 R)-3-hydroxy-5-methylthio-N-methyl-L-leucine]¹[(R)-2-(N,N-diethylamino)-2-methylpropylthio-Sar]³-cyclosporin A;

[(3 R,4 R)-3-hydroxy-5-methylthio-N-methyl-L-leucine]¹[(R)-2-(1-piperidyl)-2-methylpropylthio-Sar]³-cyclosporin A;

[(3 R,4 R)-3-hydroxy-5-methylthio-N-methyl-L-leucine]¹[(R)-3-amino-3-methylbutylthio-Sar]³-cyclosporin A;

[(3 R,4 R)-3-hydroxy-5-methylthio-N-methyl-L-leucine]¹[(R)-3-(N,N-dimethylamino)-3-methylbutylthio-Sar]³-cyclosporin A;

[(3 R,4 R)-3-hydroxy-5-methylthio-N-methyl-L-leucine]¹[(R)-3-(N,N-diethylamino)-3-methylbutylthio-Sar]³-cyclosporin A;

[(3 R,4 R)-3-hydroxy-5-methylthio-N-methyl-L-leucine]¹[(R)-3-(1-piperidyl)-3-methylbutylthio-Sar]³-cyclosporin A;

[(3 R,4 R)-3-hydroxy-5-methylthio-N-methyl-L-leucine]¹[(R)-2-(1-morpholino)ethylthio-Sar]³-cyclosporin A;

[(3 R,4 R)-3-hydroxy-5-methylthio-N-methyl-L-leucine]¹[(R)-2-(1-azetidino)ethylthio-Sar]³-cyclosporin A;

[(3 R,4 R)-3-hydroxy-5-methylthio-N-methyl-L-leucine]¹{(R)-2-[1-(4-methylpiperazino)]ethylthio-Sar}³-cyclosporin A;

[(3 R,4 R)-3-hydroxy-5-methylthio-N-methyl-L-leucine]¹{(R)-2-[1-(4-phenylpiperazino)]ethylthio-Sar}³-cyclosporin A;

[(3 R,4 R)-3-hydroxy-5-methylthio-N-methyl-L-leucine]¹{(R)-2-[1-(4-benzylpiperazino)]ethylthio-Sar}³-cyclosporin A;

[(3 R,4 R)-3-hydroxy-5-methylthio-N-methyl-L-leucine]¹{(R)-2-[1-(4-methyl-1,2,3,6-tetrahydropyridyl)]ethylthio-Sar}³-cyclosporin A;

[(3 R,4 R)-3-hydroxy-5-methylthio-N-methyl-L-leucine]¹{(R)-2-[1-(4-phenyl-1,2,3,6-tetrahydropyridyl)]ethylthio-Sar}³-cyclosporin A;

[(3 R,4 R)-3-hydroxy-5-methylthio-N-methyl-L-leucine]¹[(R)-3-(1-morpholino)propylthio-Sar]³-cyclosporin A;

[(3 R,4 R)-3-hydroxy-5-methylthio-N-methyl-L-leucine]¹[(R)-3-(1-azetidino)propylthio-Sar]³-cyclosporin A;

[(3 R,4 R)-3-hydroxy-5-methylthio-N-methyl-L-leucine]¹{(R)-3-[1-(4-methylpiperazino)]propylthio-Sar}³-cyclosporin A;

[(3 R,4 R)-3-hydroxy-5-methylthio-N-methyl-L-leucine]¹{(R)-3-[1-(4-phenylpiperazino)]propylthio-Sar}³-cyclosporin A;

[(3 R,4 R)-3-hydroxy-5-methylthio-N-methyl-L-leucine]¹{(R)-3-[1-(4-benzylpiperazino)]propylthio-Sar}³-cyclosporin A;

[(3 R,4 R)-3-hydroxy-5-methylthio-N-methyl-L-leucine]¹{(R)-3-[1-(4-methyl-1,2,3,6-tetrahydropyridyl)]propylthio-Sar}³-cyclosporin A;

[(3 R,4 R)-3-hydroxy-5-methylthio-N-methyl-L-leucine]¹{(R)-3-[1-(4-methyl-1,2,3,6-tetrahydropyridyl)]propylthio-Sar}³-cyclosporin A;

[(3 R,4 R)-3-hydroxy-5-methylthio-N-methyl-L-leucine]¹[(R)-2-methylthio-Sar]³-[4'-hydroxy-MeLeu]⁴-cyclosporin A;

[(3 R,4 R)-3-hydroxy-5-methylthio-N-methyl-L-leucine]¹[(R)-2-aminoethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-ethylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-isopropylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-tert-butylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-phenylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-benzylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-ethylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-isopropylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-tert-butylamino)ethylthio-Sar]3-[4'-hydroxy-MeLeu]⁴-cyclosporin A;

[(3 R,4 R)-3-hydroxy-5-methylthio-N-methyl-L-leucine]¹[(R)-2-(N-methyl-N-allylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-phenylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N-methyl-N-benzylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N,N-diethylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N,N-diisopropylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(N,N-diallylamino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(1-piperidyl)ethylthio-Sar]³-[4¹-hydroxy-MeLeu]⁴-cyclosporin A;

[(3 R,4 R)-3-hydroxy-5-methylthio-N-methyl-L-leucine]¹[(R)-3-aminopropylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-ethylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-isopropylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-tert-butylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-phenylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-benzylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-ethylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-isopropylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-tert-butylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-allylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-phenylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N-methyl-N-benzylamino)propylthio-Sar]³-[4'-hydroxy-MeLeu]⁴-cyclosporin A;

[(3 R,4 R)-3-hydroxy-5-methylthio-N-methyl-L-leucine]¹[(R)-2-(N,N-dimethylamino)ethylthio-Sar]3-[4'-hydroxy-MeLeu]4-cyclosporin A;

[(3 R,4 R)-3-hydroxy-5-methylthio-N-methyl-L-leucine]¹[(R)-3-(N,N-diethylamino)propylthio-Sar]3-[4'-hydroxy-MeLeu]⁴-cyclosporin A;

[(3 R,4 R)-3-hydroxy-5-methylthio-N-methyl-L-leucine]¹[(R)-3-(N,N-diisopropylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(N,N-diallylamino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(1-piperidyl)propylthio-Sar]³-[4'-hydroxy-MeLeu]⁴-cyclosporin A;

[(3 R,4 R)-3-hydroxy-5-methylthio-N-methyl-L-leucine]¹[(R)-4-aminobutylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-ethylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-isopropylamino)butylthio-Sar]³-[4'-hydroxy-Meleu]⁴-cyclosporin A;

[(3 R,4 R)-3-hydroxy-5-methylthio-N-methyl-L-leucine]¹[(R)-4-(N-tert-benzylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-phenylamino)butylthio-Sar]³-[4'-hydroxy-Meleu]⁴-cyclosporin A;

[(3 R,4 R)-3-hydroxy-5-methylthio-N-methyl-L-leucine]¹[(R)-4-(N-benzylamino)butylthio-Sar]³-[4'-hydroxy-Meleu]⁴-cyclosporin A;

[(3 R,4 R)-3-hydroxy-5-methylthio-N-methyl-L-leucine]¹[(R)-4-(N-methyl-N-ethylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-isopropylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-tert-butylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-allylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N-methyl-N-phenylamino)butylthio-Sar]³[4'-hydroxy-MeLeu]⁴-cyclosporin A;

[(3 R,4 R)-3-hydroxy-5-methylthio-N-methyl-L-leucine]¹[(R)-4-(N-methyl-N-benzylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N,N-dimethylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N,N-dilethylamino)butylthio-Sar]³-[4'-hydroxy-MeLeu]⁴-cylosporin A;

[(3 R,4 R)-3-hydroxy-5-methylthio-N-methyl-L-leucine]¹[(R)-4-(N,N-diesopropylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(N,N-diallylamino)butylthio-Sar]³-[4'-hydroxy-MeLeu]⁴-cyclosporin A;

[(3 R,4 R)-3-hydroxy-5-methylthio-N-methyl-L-leucine]¹[(R)-4-(1-piperidyl)butylthio-Sar]³-[4'-hydroxy-MeLeu]⁴-cyclosporin A;

[(3 R,4 R)-3-hydroxy-5-methylthio-N-methyl-L-leucine]¹[(R)-2-amino-2-methylpropylthio-Sar]³-[4'-hydroxy-MeLeu]⁴-cyclosporin A;

[(3 R,4 R)-3-hydroxy-5-methylthio-N-methyl-L-leucine]¹[(R)-2-(N,N-dimethylamino)-2-methylpropyl-thio-Sar]³-[4'-hydroxy-MeLeu]⁴-cyclosporin A;

[(3 R,4 R)-3-hydroxy-5-methylthio-N-methyl-L-leucine]¹[(R)-2-(N,N-diethylamino)-2-methylpropyl-thio-Sar]³-[4'-hydroxy-MeLeu]⁴-cyclosporin A;

[(3 R,4 R)-3-hydroxy-5-methylthio-N-methyl-L-leucine]¹[(R)-2-(1-piperidyl)-2-methylpropylthio- Sar]³-[4'-hydroxy-MeLeu]⁴-cyclosporin A;

[(3 R,4 R)-3-hydroxy-5-methylthio-N-methyl-L-leucine]¹[(R)-3-amino-3-methylbutylthio-Sar]³-[4'-hydroxy-MeLeu]⁴-cyclosporin A;

[(3 R,4 R)-3-hydroxy-5-methylthio-N-methyl-L-leucine]¹[(R)-3-(N,N-dimethylamino)-3-methylbutyl-thio-Sar]³-[4'-hydroxy-MeLeu]⁴-cyclosporin A;

[(3 R,4 R)-3-hydroxy-5-methylthio-N-methyl-L-leucine]¹[(R)-3-(N,N-diethylamino)-3-methylbutyl-thio-Sar]³-[4'-hydroxy-MeLeu]⁴-cyclosporin A;

[(3 R,4 R)-3-hydroxy-5-methylthio-N-methyl-L-leucine]¹[(R)-3-(1-piperidyl)-3-methylbutylthio- Sar]³-[4'-hydroxy-MeLeu]⁴-cyclosporin A;

[(3 R,4 R)-3-hydroxy-5-methylthio-N-methyl-L-leucine]¹[(R)-2-(1-morpholino)ethylthio-Sar]³-[4'-hydroxy-MeLeu]⁴-cyclosporin A;

[(3 R,4 R)-3-hydroxy-5-methylthio-N-methyl-L-leucine]¹[(R)-2-(1-azetidino)ethylthio-Sar]³-[4'-hydroxy-MeLeu]⁴-cyclosporin A;

[(3 R,4 R)-3-hydroxy-5-methylthio-N-methyl-L-leucine]¹{(R)-2-[1-(4-methylpiperazino)]ethylthio-Sar}³-[4'-hydroxy-MeLeu]⁴-cyclosporin A;

[(3 R,4 R)-3-hydroxy-5-methylthio-N-methyl-L-leucine]¹{(R)-2-[1-(4-phenylpiperazino)]ethylthio-Sar}³-[4'-hydroxy-MeLeu]⁴-cyclosporin A;

[(3 R,4 R)-3-hydroxy-5-methylthio-N-methyl-L-leucine]¹{(R)-2-[1-(4-benzylpiperazino)]ethylthio-Sar}³-[4'-hydroxy-MeLeU]⁴-cyclosporin A;

[(3 R,4 R)-3-hydroxy-5-methylthio-N-methyl-L-leucine]¹{(R)-2-[1-(4-methyl-1,2,3,6-tetrahydropyridyl)]ethylthio-Sar}³-[4'-hydroxy-MeLeu]⁴-cyclosporin A;

[(3 R,4 R)-3-hydroxy-5-methylthio-N-methyl-L-leucine]¹{(R)-2-[1-(4-phenyl-1,2,3,6-tetrahydropyridyl)]ethylthio-Sar}³-[4'-hydroxy-MeLeu]⁴-cyclosporin A;

[(3 R,4 R)-3-hydroxy-5-methylthio-N-methyl-L-leucine]¹[(R)-3-(1-morpholino)propylthio-Sar]³-[4'-hydroxy-MeLeu]⁴-cyclosporin A;

[(3 R,4 R)-3-hydroxy-5-methylthio-N-methyl-L-leucine]¹[(R)-3-(1-azetidino)propylthio-Sar]³-[4'-hydroxy-MeLeu]⁴-cyclosporin A;

[(3 R,4 R)-3-hydroxy-5-methylthio-N-methyl-L-leucine]¹{(R)-3-[1-(4-methylpiperazino)]propylthio-Sar}³-[4'-hydroxy-MeLeu]⁴-cyclosporin A;

[(3 R,4 R)-3-hydroxy-5-methylthio-N-methyl-L-leucine]¹{(R)-3-[1-(4-phenylpiperazino)]propylthio-Sar}³-[4'-hydroxy-MeLeu]⁴-cyclosporin A;

[(3 R,4 R)-3-hydroxy-5-methylthio-N-methyl-L-leucine]¹{(R)-3-[1-(4-benzylpiperazino)]propylthio-Sar}³-[4'-hydroxy-MeLeu]⁴-cyclosporin A;

[(3 R,4 R)-3-hydroxy-5-methylthio-N-methyl-L-leucine]¹{(R)-3-[1-(4-methyl-1,2,3,6-tetrahydropyridyl)]propylthio-Sar}³-[4'-hydroxy-MeLeu]⁴-cyclosporin A; and

[(3 R,4 R)-3-hydroxy-5-methylthio-N-methyl-L-leucine]¹{(R)-3-[1-(4-methyl-1,2,3,6-tetrahydropyridyl)]propylthio-Sar}³-[4'-hydroxy-MeLeu]⁴-cyclosporin A; or a pharmaceutically acceptable salt of any of said compounds.

14. A method for the treatment of a retrovirus, said method comprising administering to a host for the purpose of said treatment an effective amount of a cyclosporin compound of formula (I) or a salt thereof according to claim 1.

15. A method of inhibiting the growth of retroviral-infected cells which comprises administering an effective amount of a cyclosporin compound of formula (I) or a salt thereof according to claim 1.

16. The method according to claim 15, wherein the retrovirus is HIV.

17. A method for treatment of a subject which comprises administering to the subject an effective amount of a cyclosporin compound of formula (I) or a salt thereof according to claim 1 effective to reduce the likelihood of a subject developing AIDS.

* * * * *

UNITED STATES PATENT AND TRADEMARK OFFICE
CERTIFICATE OF CORRECTION

PATENT NO. : 5,977,067
DATED : November 2, 1999
INVENTOR(S) : Michel Evers, et. al.

It is certified that error appears in the above-identified patent and that said Letters Patent is hereby corrected as shown below:

On the Title Page, Item [75], in the Inventors, line 1, "La Queue en Brie" should read --La Queue-en-Brie--; and line 9, "Bures sur Yvette" should read --Bures-sur-Yvette--.

In Claim 1, col. 28, line 54, before "a halogen", delete "selected from".

In Claim 1, col. 28, lines 61-62, "unsatured" should read --unsaturated--.

In Claim 1, col. 28, line 65, "unsatured" should read --unsaturated--.

In Claim 3, col. 30, line 6, "Alk-R'" should read --Alk-R'--.

In Claim 10, col. 31, line 54, "(V" should read --(V)--.

In Claim 13, col. 32, line 57, "ethylam ino" should read --ethylamino--.

In Claim 13, col. 33, lines 11-12, "Sar] 3-cycosporin" should read --Sar]$^3$-cyclosporin--.

In Claim 13, col. 33, line 57, "ropylthio-" should read --propylthio--.

In Claim 13, col. 34, line 42, "Sar]3" should read --Sar]$^3$--.

In Claim 13, col. 36, line 32, "ethylthio-Sar]3" should read --ethylthio-Sar]$^3$--.

UNITED STATES PATENT AND TRADEMARK OFFICE
CERTIFICATE OF CORRECTION

PATENT NO. : 5,977,067
DATED : November 2, 1999
INVENTOR(S) : Michel Evers, et. al.

It is certified that error appears in the above-identified patent and that said Letters Patent is hereby corrected as shown below:

In Claim 13, col. 36, line 53, "[41-" should read --[4'- --.

In Claim 13, col. 37, line 31, "Sar]3-" should read --Sar]$^3$- --.

In Claim 13, col. 37, line 32, "MeLeu]4-" should read --MeLeu]$^4$- --.

In Claim 13, col. 37, line 34, "Sar]3-" should read --Sar]$^3$- --.

In Claim 13, col. 37, line 57, "Meleu" should read --MeLeu--.

In Claim 13, col. 37, line 59, "N-tert-benzylamino" should read --N-tert-butylamino--.

In Claim 13, col. 37, line 64, "Meleu" should read --MeLeu--.

In Claim 13, col. 37, line 67, "Meleu" should read --MeLeu--.

In Claim 13, col. 38, line 27, "diesopropylamino" should read --diisopropylamino--.

In Claim 13, col. 39, line 9, "MeLeU" should read --MeLeu--.

Signed and Sealed this

Twenty-seventh Day of February, 2001

Attest:

NICHOLAS P. GODICI

*Attesting Officer*   *Acting Director of the United States Patent and Trademark Office*